United States Patent [19]
Li et al.

[11] Patent Number: 5,955,361
[45] Date of Patent: Sep. 21, 1999

[54] P GENE PROMOTER CONSTRUCTS FOR FLORAL-TISSUE PREFERRED GENE EXPRESSION

[75] Inventors: Xianggan Li, Newark, Del.; Ben Bown, Des Moines; Thomas Peterson, Ames, both of Iowa

[73] Assignee: Pioneer Hi-Bred International, Inc., Des Moines, Iowa

[21] Appl. No.: 08/754,282

[22] Filed: Nov. 20, 1996

[51] Int. Cl.[6] .............................. A01H 4/11; A01H 3/00; C07H 21/04; C12N 5/10
[52] U.S. Cl. .................... 435/419; 800/205; 800/250; 536/24.1
[58] Field of Search ............................ 435/419; 800/205, 800/250; 536/24.1

[56] References Cited

PUBLICATIONS

An, G., Mitra, A., Choi, H.K., Costa, M.A., An, K., Thornburg, R.W., and Ryan, C.A. (1989). Functional analysis of the 3' control region of the potato wound–inducible proteinase inhibitor 11 gene. Plant Cell 1, 115–122.

An, W. and Wensink, P.C. (1995) Three protein binding sites from an enhancer geneser that regulates sex– and fat body–specific transcription of Drosophila yolk protein genes. The EMBO Journal 74 (6), 1221–1230.

Athma, P., Grotewold, E. and Peterson T. (1992). Insertional mutagenesis of the maize P gene by intragenic transpostion of Ac. Genetics 131:199–209.

Athma, P. and Peterson, T. (1991) Ac induces homologous recombination at the maize P locus. Genetics 128, 163–173.

Bingham, P.M. and Zachar, Z., (1989) Retrotransposon and the FB transposon from Drosophila melanogaster. In Berg, D. E. and Howe, M. M. (eds.) Mobile DNA, American Society for Microbiology. pp. 485–502.

Brink,R.A. and Nilan,R.A. (1952) The relation between light variegated and medium variegated pericarp in maize. Genetics 37:519–544.

Benfey, P.N., and Chua, N.–H. (1989) Regulated genes in transgenic plants. Science 244, 174–181.

Bowen, B. (1992). Anthocyanin genes as visual markers in transformed maize tissues. In Gallagher, S.R. (ed.) GUS Protocols: Using the GUS gene as a reporter of gene expression. Academic Press. San Diego, California. pp. 163–177.

Bureau T. E. and Wessler S. R. (1992) Tourist: A large family of small inverted repeat elements frequently associated with maize genes. The Plant Cell 4:1283–1294.

Carlson, D. P. and Ross, J. (1983) Human $\beta$–globin promoter and coding sequences transcribed by RNA polymerase III. Cell 34:857–864.

Chen, J., Greenblatt, I.M., and Dellaporta, S.L. (1987) Transposition of Ac from the P locus of maize into unreplicated chromosomal sites. Genetics 117: 101–108.

Chen, J., Greenblatt, I.M., and Dellaporta, S.L. (1992) Molecular analysis of Ac transposition and DNA replication. Genetics 130:665–676.

Das. O.P., Messing, J. (1994) Variegated phenotype and developmental methylation changes of a maize allele originating from epimutation. Genetics 136:1121–1141.

De Block, M., Botterman, J., Vandewile, M., Docky, J., Thoen, C., Gossele, V., Rao Movva, N., Thompson, C., Van Montagu, M., and Leemans, J. (1987) Engineering herbicide resistance in plants by expression of a detoxifying enzyme. EMBO Journal 6:125–135.

Dennis, E., Gerlach, W., Pryor, A., Bennetzen, J., Inglis, A., Llewellyn, D., Sachs, M., Ferl, R. and Peacock, W. (1984) Molecular characterization of the maize Adhl gene. Nucl. Acids Res. 12: 3983–3990.

Emerson, R.A. (1917) Genetical studies of variegated pericarp in maize. Genetics 2:1–35.

Fromm, M. (1994) Production of transgenic maize plants via microprojectile–mediated gene transfer. In Freering, M. and Walbot, V. (eds), The Maize Handbook. Spring–Verlag, New York. pp. 677–684.

Gallie, D. R. and Young T.E. (1994) The regulation of gene expression in transformed maize aleurone and endosperm protoplasts. Plant Physiol. 106:929–939.

Gordon–Kamm, W. J., Spencer,M., Mangano, M.L., Adams, T.R., Daines, R.J., Start, W.G., O'Brien, J.V., Chambers, S.A., Adams, W.R. Jr., Willetts, N.G., Rice,T.B., Mackey, K.J., Krueger, R.W., Kausch, A.P. and Lemaux, P.G. (1990) Transformation of Maize Cells and Regeneration of Fertile Transgenic Plants. The Plant Cell 2:603–618.

Grotewold E., Drummond B.J., Bowen B., and Peterson T. (1995) The myb–homologous P gene controls phlobaphene pigmentation in maize floral organs by directly activating a flavonoid biosynthetic gene subset. Cell 76:543–553.

Grotewold, E., Athma, P., and Peterson, T. (1991) Alternatively spliced products of the maize P gene encode proteins with homology to the DNA binding domain of Myb–like transcription factors. Proc. Natl. Acad. Sci. USA 88:4587–4591.

Hull, M. W., Erickson, J., Johnston, M. and Engelke, D. R. (1994) tRNA genes as transcriptional repressor elements. Molecular and Cellular Biology 14:1266–1277.

Jefferson, R.A., Burgess, S.M. and Hirsh, D. (1986) β–Glucuronidase from Escherichia coli as a gene fusion marker. Proc. Natl. Acad. Sci. USA 83:8447–8451.

Klein, T.M., Kornstein, L., Sanford, J.C., and Fromm, M.E. (1989) Genetic transformation of maize cells by particle bombardment. Plant Physiol. 91: 44044.

Konieczny, A., Voytas, D.F., Cummings, M.P. and Ausubel, F.M. (1991) A superfamily of Arabidopsis thaliana retrotransposons. Genetics 127 (4): 801–809.

Kyozuka, J., Olive,M., Peacock, W.J., Dennis, E.S. and Shimamoto K. (1994) Promotor Elements Required for Development Expression of the Maize Adhl gene in Transgenic Rice. The Plant Cell 6:799–810.

Lecheit, C., Peterson, T., Laired, A., Chen, J., Dellaporta, S., Dennis, E., Peacock, W.J., and Starlinger, P. (1989) Isolation and molecular analysis of the maize P locus. Mol. Gen. Genet. 219:225–234.

Ludwig, S.E., Bowen, B., Beach, L., and Wessier, S.R. (1990). A regulatory gene as a novel visible marker for maize transfornation. Science 246:449–450.

Lund G., Das O.P., and Messing J. (1995) Tissue–specific DNase I–sensitive sites of the maize P gene and their changes upon epimutation. The Plant Journal 7(5):797–807.

Moreno, M.A., Chen, J., Greenblatt, I., and Dellaporta, S.L. (1992) Reconstitutional mutagenesis of the maize P gene by short–range Ac transpostions. Genetics 131:939–956.

Peterson, T. (1990) Intragenic transpostion of Ac generates a new allele of the maize P gene. Genetics 126:469–476.

Radicella J.P., Brown D., Tolar L.A. and Chandler V.L. (1992) Allelic diversity of the maize B regulatory gene: different leader and promoter sequences of two B alleles determine distinct tissue specificities of anthocyanin production. Genes & Development 6:2152–2164.

Styles, E. D. and Ceska 0. (1977) The genetic control of flavonoid synthesis in maize. Can. J. Genet. Cytol. 19:289–302.

Styles, E. D. and Ceska 0. (1981) P and R control of flavonoids in Bronze coleptiles of maize. Can. J. Genet. Cytol. 23:691–704.

Su,T. Z. and El–Gewely, M.R. (1988) A multisite–directed mutagenesis procedure using T7 DNA polymerase: Application for reconstructing a mammalian gene. Gene 69:81–89.

Linger, E., Parsons, R.L.., Schmidt, R.J., Bowen, B., and Roth, B.A. (1993) Dominant negative mutants of Opaque2 suppress transactivation of a 22–IcD zein protein by opaque 2 in maize endosperm cells. Plant Cell 5: 831–841.

Voytas D. F., Cummings, M.P., Konieczny,A., Ausubel, F.M. and Rodermel, S.R. (1992) Copia–like retrotransposons are ubiquitous among plants. Proc. Natl. Acad. Sci. USA. 31: 7124–7128.

Walker E. L., Robbins,T. P., Bureau,T. E., Kermicle, J., and Dellaporta, S. L. (1995) Transposon–mediated chromosomal rearrangements and gene duplications in the formation of the maize R–r complex. The EMBO Journal 14: 2350–2363.

Weiher, H., Konig, M., Gruss, P. (1983) Multiple point mutations affecting the Simian virus 40 enhancer. Science 219: 626–631.

Christensen, et al. (1992). Maize polyubiquitin genes: structure, thermal perturbation of expression and transcript splicing, and promoter activity following transfer to protoplasts by electroporation. Plant Mol. Biol. 18:675–689.

Odell, et al. (1985). Identification of DNA sequences required for activity of the cauliflower mosaic virus 35S promoter. Nature 313: 810–812.

Depicker, et al. (1982). Nopaline synthase: transcript mapping and DNA sequence. J. Mol. Appl. Genet. 1:561–573.

*Primary Examiner*—Ponnathapura Achutamurthy
*Assistant Examiner*—Phuong T. Bui

[57] ABSTRACT

This invention provides a transcriptional regulatory region of a gene which will be utilized to direct tissue-specific gene expression in plants such that a selective advantage is conferred upon said plants. The present invention relates to the isolation, characterization and utilization of a transcriptional regulatory region of a plant gene which is expressed in a floral tissue-specific manner. The transcriptional control region of said gene is demonstrated to drive gene expression in a floral-specific manner in vivo using transgenic plants.

21 Claims, 13 Drawing Sheets

| PLASMIDS | EVENTS | PLANTS | GUS+ (%) |
|---|---|---|---|
| Pb::GUS | 12 | 76 | 18 |
| P1.0b::GUS | 15 | 160 | 77 |
| P1.2b::GUS | 15 | 94 | 54 |
| SL100 | 13 | 83 | 8 |
| SL101 | 14 | 82 | 6 |
| SL102 | 2 | - | - |
| SL103 | 20 | 120 | 5 |
| TOTAL | 91 | 615 | |

FIG. 12

P GENE PROMOTER CONSTRUCTS FOR FLORAL-TISSUE PREFERRED GENE EXPRESSION

BACKGROUND OF THE INVENTION

1. Field of the Invention

This invention relates generally to mechanisms of gene expression in plants and more specifically to regulation of expression of genes in plants in a "floral-preferred" manner. Regulation of expression is achieved using at least one of several transcriptional regulatory units capable of driving expression of genes within floral tissues of a plant. Said transcriptional regulatory unit will ultimately be utilized for driving expression of genes that confer a selective advantage to plants.

2. Description of the Related Art

Over the past decade, the valuable method of introducing foreign genes into plants has been used to study promoter strength and tissue-preferred gene expression (Benfey and Chua, 1989). Despite prolonged and substantial effort by many laboratories, development of genetic transformation techniques for maize has been difficult to achieve (Gordon-Kamm et al., 1990). To understand the mechanisms regulating tissue-preferred expression and the cis-acting factors interacting with tissue-preferred elements, a necessary step is to define the promoter regions controlling expression. Transgenic plants are a useful tool in such studies. In general, these types of studies have not been possible using transgenic maize plants because of the absence of a routine transformation system (Kyozuka et al., 1994). This invention illustrates the feasibility and importance of using transgenic maize in the study of promoter regulation in a homologous system. Transcriptional control elements which drive "tissue-general" or "constitutive" gene expression in plants have been described. These include the promoters of the Agrobacterium nopaline synthase gene (Depicker, et al. 1982) and the maize ubiquitin gene (Christensen, et al. 1992). Other promoters have been well characterized and utilized for driving constitutive gene expression in transgenic plants [e.g., CaMV 35S (Odell et al. 1985)]. There exists both an increasing interest in co-transforming plants with multiple plant transcription units and a realization of several potential problems associated with this technique. In order to protect plants from certain pests, pathogens, adverse weather conditions or to provide growth or other survival advantages to a plant, it is useful to direct gene expression to certain tissues of a plant. In this manner, gene expression may be maintained at a low or non-existent level in tissues in which expression of said gene could prove detrimental to the plant or may result in a drain on the plant's energy resources. It is, therefore, considered important by those skilled in the art to develop transcriptional regulatory units (including but not limited to promoters, enhancers and repressors) useful in limiting gene expression to certain tissues of a plant.

The P gene encodes a myb-like transcription activator, controlling phlobaphene pigmentation in maize floral organs by directly activating a flavonoid biosynthetic gene subset (Grotewold et al., 1991 & 1994). The floral tissues in which the P gene is expressed include but are not limited to kernel pericarp, the lemma, palea and glumes of the female flower, and similar organs of the male flower. Due to its conspicuous red pigmentation phenotype, the P gene has been the object of extensive genetic analysis since the pioneering work of Emerson (1917). The maize P alleles are usually named based on pigmentation in these two tissues, e.g., P-rr: red pericarp and red cob; P-wr: white pericarp and red cob; P-rw: red pericarp and white cob; P-ww: white pericarp and white cob. Despite the extensive and long-standing genetic studies of the P gene, little is known regarding the mechanism of P gene regulation of tissue-preferred phlobaphene pigmentation in certain floral tissues (Styles, & Ceska, 1977). The P-vv allele, which specifies variegated pericarp and cob pigmentation and contains the transposable element Ac inserted in the P-rr allele (Lechelt et al., 1989), has been used to study Ac transpositional mutagenesis (Athma et al., 1992) and the transpositional mechanisms (Chen et al., 1987 and 1992). Molecular mapping and DNA sequence analyses have shown that reinsertions were clustered in two regions, the 1.3 kb sequences immediately 5' of the transcription start site and an upstream region corresponding to a 1.2-kb SalI fragment, localized 4853 bp upstream of the TSS (Moreno et al., 1992). Although the insertions in the 1.2-kb SalI fragment are approximately 5 kb upstream from the TSS, a lightly to very lightly variegated phenotype is observed in plants with such insertions. It was suggested that these insertions might affect the activity of cis-acting sequences, such as enhancer elements required for P-rr activity. If such distal enhancers exist, the P-rr promoter would represent the largest plant promoter reported to date (Moreno et al, 1992). A new allele, P-pr, was found to arise from epimutation of P-rr (Das and Messing, 1994). P-rr specifies a red pericarp and red cob glumes and P-pr specifies patterned pericarp and red cob. Reduction in red pigmentation of plants expressing P-pr was associated with decrease in P-pr mRNA levels, possibly due to greater methylation in the promoter or elsewhere in the P-pr gene. The previously mentioned upstream 1.2 kb region has been demonstrated to affect expression of the P-rr gene. Alteration of the 1.2 kb region have been shown to include insertions, methylation, and tissue-specific changes in chromatin structure. It was therefore hypothesized that this region may contain cis-acting elements important to the tissue-specific pattern of expression observed in plant tissues (Lund et al., 1995).

To understand the regulatory role of the upstream 1.2-kb SalI region and to determine which regions of the P-rr promoter direct floral specificity to the P-rr gene, we tested DNA constructs comprising regions of the P-rr promoter operably linked to a reporter gene, the b-glucuronidase gene (GUS), in transient assays (Martin, T., et al. In S. R. Gallagher (ed.), *GUS Protocols: Using the GUS gene as a reporter of gene expression*, p. 23–43). These constructs were also tested by transformation of plant cell cultures and the subsequent generation of stable transgenic plants. It is demonstrated that the primary determinants of maize P-rr floral-specificity resides in the basal 500 bp region immediately 5' of the transcription start site (TSS). Tissue specificity and a precise developmental pattern of P gene promoter-driven GUS gene expression in stable transgenic maize was observed in floral tissues including pericarps, cob glumes, silk, and husks without any detectable expression in roots, stems, and leaves. Gene expression driven by this region of the promoter, while floral-preferred, is at low levels. Expression vectors comprising preferred regions of the P promoter were constructed and certain regions demonstrated to function as enhancer elements. The enhancer elements are separated by up to 3.6 kb and possibly function as long distance enhancer elements. The results of the functional assays are consistent with predictions from Ac insertional mutagenesis experiments (Moreno et al., 1992), P-pr methylation pattern (Das and Messing, 1994), and DNase I sensitivity assays (Lund et al., 1995). These data underscore the importance of these sequences for P-rr expression.

There is a need in the art for novel transcriptional regulatory elements which are capable of driving floral-preferred gene expression in plants. It is considered important by those skilled in the art to continue to provide tissue-preferred transcription units capable driving expression of genes that confer resistance to plant pathogens, pests, herbicides, or adverse weather conditions including but not limited to cold, heat, and flooding as well as genes which influence growth of or yield from said plants. The inventions described within this application may be utilized to drive floral-preferred gene expression in plants, and therefore, are considered important to those skilled in the art.

BRIEF DESCRIPTION OF THE DRAWINGS

FIG. 12 Summary of stable transgenic callus lines obtained and T0 plants regenerated from P::GUS transformants. The number of selected stable callus events (Events), plants regenerated from all events (Plants), and the percentage of the plants demonstrating GUS staining (GUS+), are shown in Column 2, 3, and 4, respectively.

SUMMARY OF THE INVENTION

Figure 1:
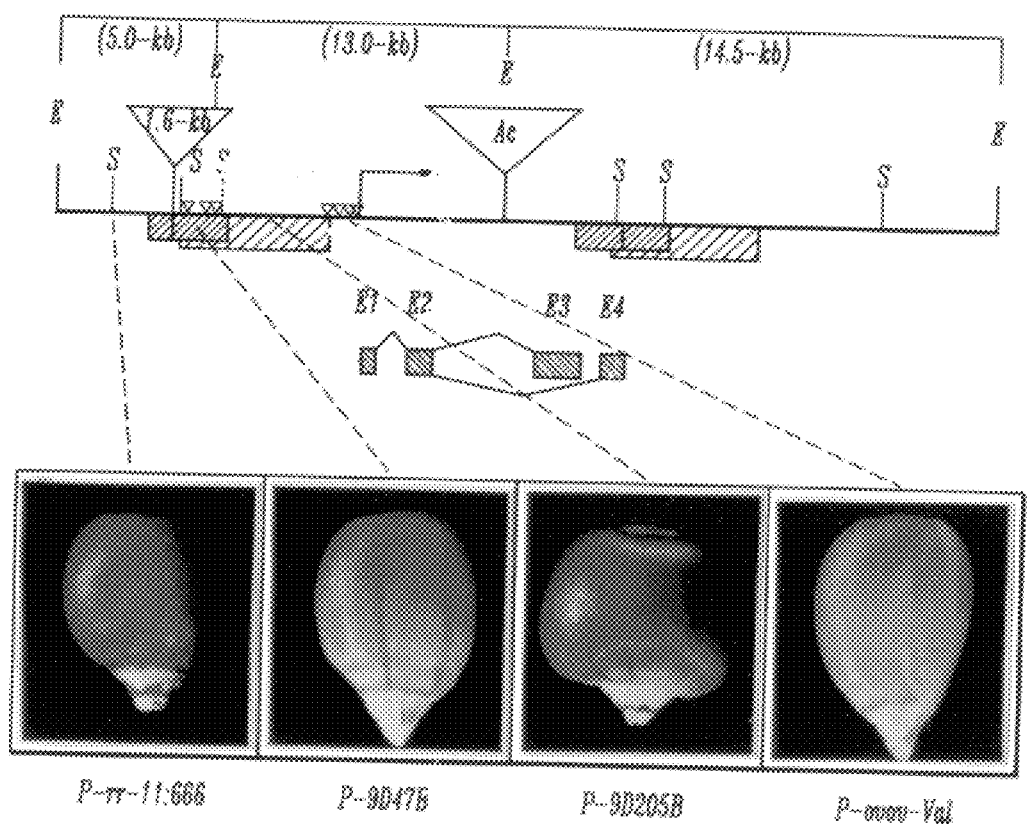
FIG. 1 Restriction map of the P-rr locus. The 5.2-kb direct repeats (hatched boxes) flanking the P gene, and 1.2-kb direct repeat sequences (dotted boxes) are indicated (Athma et al., 1992). The big triangle indicates the insertion site of the transposable element Ac in P-vv allele. A 1.6-kb insertion 5 kb upstream of the transcriptional start site is indicated by the horizontal triangle. Restriction sites for SalI (S) and EcoRI (E) are indicated although all sites are not shown. EcoRI (E) restriction fragments are indicated. The structure of the 1.8 kb P-rr transcript is shown with filled boxes (Athma et al., 1992). Exons are indicated by E1, E2, E3, and E4. The small triangles represent Ac insertions mapped by Moreno et al. (1992). Photographs illustrate the phenotypes resulting from insertion of Ac at sites indicated by dashed lines. Plants producing these kernels were heterozygous with a W22 background.

This invention provides a transcriptional regulatory region of a gene useful for directing direct tissue-preferred gene expression in a plant. Said transcriptional regulatory region is preferably utilized to drive expression of a gene encoding a gene product that confers a selective advantage upon a plant in which said gene product is expressed. There exists a need in the art for transcriptional regulatory elements of plant genes which drive expression of said genes specifically or preferably within certain tissues of a plant. Such transcriptional units are defined within this application to function in a "tissue-preferred" manner. The present invention relates to the isolation, characterization and utilization of a transcriptional regulatory region of a plant gene which is expressed in a floral tissue-preferred manner. Transient assays reveal that preferred regions of the transcriptional regulatory region of said gene expressed in a floral tissue-preferred manner selectively drive expression of genes in floral tissues of maize. The transcriptional control region of said gene is further demonstrated to drive gene expression in a floral-preferred manner in vivo within transgenic plants.

It is an object of the invention to provide DNA molecules which represent genes or fragments thereof which are expressed in a floral tissue-preferred manner.

It is also an object of the invention to provide a DNA molecule representing a transcriptional regulatory region of a gene which is expressed in a floral tissue-preferred manner.

It is yet another object of the invention to provide a DNA molecule capable of directing reporter or effector gene expression to floral tissues of maize.

It is also an object of the invention to provide a reporter construct useful for testing the ability of said floral tissue-preferred transcriptional regulatory region to drive expression of a reporter gene in a floral tissue-preferred manner in vivo.

It is another object of the invention to provide a method useful for testing the ability of said transcriptional regulatory region to drive expression of a reporter gene in a floral tissue-preferred manner in planta.

It is further an object of the invention to provide expression vectors useful for driving expression of an effector gene in a floral tissue-preferred manner in planta.

It is a still further object of the invention to provide a DNA molecule which will confer a selective advantage to plants transformed with said DNA molecule.

It is an object of the invention to provide plants comprising mutated alleles of a gene expressed in a floral tissue-preferred manner.

It is yet another object of the invention to provide a DNA molecule which directs floral tissue-preferred effector gene expression in plants resulting in resistance against plant pathogens, pests, herbicides, or adverse weather conditions or confers a growth advantage to plants.

It is also an object of the invention to provide a method for generating a transgenic plant transformed with a floral tissue-preferred expression vector which directs expression of an effector gene in the floral tissues of said plant.

In one embodiment, the present invention comprises maize plants having the transposable element Ac inserted into at least one site of the gene promoter such that a plant having an altered phenotype results.

In another embodiment, the present invention comprises a DNA fragment comprising a region of the P gene promoter having the transposable element Ac inserted into at least one site within the promoter that is useful in directing floral tissue-preferred gene expression.

In another embodiment, the present invention comprises a DNA fragment comprising a region of the P gene promoter capable of directing floral tissue-preferred gene expression.

In still another embodiment, the present invention comprises a DNA molecule comprising a floral tissue-preferred gene promoter operably linked to a reporter or effector gene.

In another embodiment, the present invention comprises a DNA molecule comprising a floral tissue-preferred gene promoter operably linked to an effector gene, expression of said effector gene within a plant conferring a selective advantage to said plant.

In another embodiment, the present invention comprises a DNA molecule comprising a floral tissue-preferred gene promoter operably linked to an effector gene, expression of said effector gene conferring resistance of maize to ear-mold infection.

In yet another embodiment, the present invention comprises a method for generating a transgenic plant that express an effector gene under the transcriptional control of a floral tissued-preferred transcriptional regulatory unit such that expression of said effector gene in said floral tissues confers a selective advantage to said transgenic plant.

DETAILED DESCRIPTION OF THE INVENTIONS

Within this application, a transcriptional regulatory region is defined as any element involved in regulating transcription of a gene, including but not limited to promoters, enhancers and repressors. Said transcriptional regulatory region may alternatively be referred to as a gene promoter.

A gene promoter is defined as any element involved in regulating transcription of a gene, including but not limited to promoters, enhancers and repressors.

A gene expressed in a tissue-preferred manner is that which demonstrates a greater amount of expression in one tissue as opposed to one or more second tissues in a plant specimen.

A gene defined as floral tissue-preferred or floral tissue-preferred defines a gene which is expressed at a higher level in the floral tissues of a plant as opposed to other tissues in said plant.

The floral tissue of a plant includes but is not limited to kernel pericarp, the lemma, palea, and glumes of the female flower, and similar organs of the male flower.

A regenerable culture is defined as a cell or tissue culture that can be manipulated so as to allow regeneration of plants.

Plant refers to a photosynthetic organism including algae, mosses, ferns, gymnosperms, and angiosperms as well as cultures thereof. Plant may further refer to the seed of a plant.

A plant cell includes any cell derived from a plant, including callus as well as protoplasts, and embryonic and gametic cells.

Transgenic plant defines a plant in which a gene has been added to the germline of said plant.

Transformation refers to a method of introduction of DNA into a cell. Said method of introduction may include but is not limited to particle bombardment, lipofection, electroporation, viral or bacterial vector-mediated, and calcium phosphate mediated techniques.

A mature plant is defined as a plant in which normal development of all vegetative and reproductive organs has occurred.

A gene product that confers a selective advantage to a plant is defined as any gene product which, upon expression in said plant, confers increased growth rate, yield of product or resistance to threats to said plant's ability to thrive including but not limited to pathogens, pests, adverse weather conditions, and herbicides relative to plants that do not express said gene product.

An assayable product includes any product encoded by a gene which is detectable using an assay. Furthermore, the detection and quantitation of said assayable product is directly proportional to the level of expression of said gene.

A DNA construct is defined a plasmid, virus, autonomously replicating sequence, phage or linear segment of a single- or double-stranded DNA or RNA derived from any source.

A reporter construct is defined as a subchromosomal and purified DNA molecule comprising a gene encoding an assayable product.

An expression vector is defined as a DNA construct comprising at least one gene which, upon transfection into a cell, results in expression of the product of said gene.

The term operably linked refers to the combination of a first nucleic acid fragment representing a transcriptional control region functionally joined to a second nucleic acid fragment encoding a reporter or effector gene such that expression of said reporter or effector gene is influenced by the presence of said transcriptional control region.

To isolate transcriptional regulatory regions useful for driving tissue-preferred expression of effector genes in plants, it is necessary to identify genes which demonstrate a tissue-preferred pattern of expression in plants. One method of identification is PCR-based differential display analysis (Liang, et al. 1992. Science 257:967). This methodology involves the use of random oligonucleotide primers, PCR-amplification of RT-cDNA and comparison of patterns of expression between at least two samples. Said samples may include but are not limited to different types of cells or tissues, cells or tissues in various stages of development, or cells or tissues which have been exposed to various chemicals or conditions which may result in a change in gene expression said cells or tissues. Non-identical DNA banding patterns of DNA amplified from said samples indicate a difference in gene expression between samples. DNA corresponding to the bands which exhibit said non-identical DNA banding patterns are cloned and utilized to identify the genes to which the DNA bands correspond. An alternative method involves the use of subtractive hybridization (Lee, et al. 1991. Proc. Natl. Acad. Sci. U.S.A. 88:2825). This methodology involves the hybridization of cDNA (antisense) of sample A and biotinylated-RNA of sample B. Biotinylated-RNA molecules of sample B representing genes expressed in both samples hybridize to the complementary cDNA molecules of sample A and are destroyed by subsequent enzymatic treatment. Following purification of the remaining biotinylated RNA molecules of sample B, a cDNA library is constructed using said remaining biotinylated RNA of sample B. The clones of said cDNA library represent genes which are preferentially expressed in sample B. A further method is by screening of a cDNA library of a first sample using labeled RNA representing a second sample. Clones of said cDNA library of said first sample which do not hybridize to said labeled RNA of said second sample represent mRNA species which are not expressed in said second sample. Alternatively, several libraries may be individually screened using labeled RNA from several separate samples. If said samples are different tissues of a plant, altered patterns of hybridization in one sample as compared to another sample indicates a tissue-preferred pattern of gene expression. cDNA clones isolated in the above-described manner will represent mRNA species which are preferentially expressed in a sample or a group of samples.

It is then necessary to confirm that a cDNA isolated by any of the above-described techniques or any other technique resulting in the isolation of potentially tissue-preferred plant genes is expressed in a tissue-preferred manner. RT-PCR is a method by which mRNA represented by a potentially tissue-preferred cDNA is amplified from a cell or tissue of interest (Berchtold, 1989. Nuc. Acids Res. 17:453). Amplification of said mRNA from several different tissues allows for a comparison to be made and the relative level of expression of mRNA of said potentially tissue-preferred plant gene to be determined. Another method which may be utilized to determine the level of gene expression in a plant cell or plant tissue is RNase protection assays (Melton, et al. 1984. Nuc. Acids Res. 12:7035). RNA from the samples to be compared is hybridized to a labeled antisense RNA probe generated from a cDNA representing a mRNA of a plant gene potentially expressed in a tissue-preferred manner. This is followed by the addition of RNase. All RNA which has hybridized to said labeled antisense RNA probe is protected from degradation (termed protected transcripts) by the RNase while mRNA which has not hybridized to said antisense labeled RNA probe is degraded. The products are then separated by gel electrophoresis and protected transcripts detected using detection methods including but not limited to autoradiography. The relative intensity of the band corresponding to said protected transcripts is proportional to the level of expression that protected RNA species in each tissue. A still further method with which tissue-preferred expression may be determined by northern blot analysis (Alwine, et al. 1977. Proc. Natl. Acad. Sci. U.S.A. 74:5350). RNA isolated from a sample of interest is isolated and separated by gel electrophoresis. The separated RNA species are then transferred to a membrane and probed with a labeled nucleic acid probe which is complementary to RNA representing a gene of interest. Hybridization is detected using a detection method including but not limited to autoradiography. The intensity of the band corresponding to RNA representing a gene of interest is determined and is proportional to the level of gene expression in each sample. A tissue-preferred gene is identified by increased hybridization in one tissue as compared to a second tissue of a plant.

It is then desirable to isolate the transcriptional regulatory region responsible for driving expression of said gene of interest in a tissue-preferred manner. This region may be isolated by several methods including but not limited to amplification of a region of DNA comprising said transcriptional regulatory region. Said DNA is amplified from genomic DNA maintained as a genomic DNA library in a cloning vector including but not limited to phage, plasmids, cosmids, yeast artificial chromosomes (YAC) or any other vector capable of harboring fragments of chromosomal DNA. Said transcriptional regulatory region of said gene expressed in a tissued-preferred manner may be isolated by amplification of the genomic sequences encoding the cDNA sequence. Two oligonucleotide primers, the first of which comprising sequence complementary to a region within the nucleotide sequence of said cloning vector and the second of which comprising sequence complementary to a 5' region of said cDNA encoding a gene expressed in a tissue-preferred manner, are utilized in a PCR reaction. The template for said PCR reaction comprises a portion of said genomic DNA library. Amplification products may include but are not limited to DNA comprising a 5' region of said gene of interest, a 3' region of said gene of interest that may comprise a 3' untranslated region, or fragments thereof. DNA sequencing of each amplified product results in identification of those clones comprising a potential transcriptional regulatory region (Frohman, et al. 1998. Proc. Natl. Acad. Sci. U.S.A. 85:8998). A further method for isolation of the transcriptional region of a gene expressed in a tissued-preferred manner includes utilization of the cDNA or fragment thereof encoding the gene of interest as a cDNA probe to screen said genomic DNA library by hybridization. Clones which demonstrate hybridization to said cDNA probe are isolated and characterized by restriction enzyme mapping and nucleotide sequence analysis.

To construct expression vectors useful for testing the transcriptional regulatory region of a gene expressed in a tissue-preferred manner, the elements responsible for said ability to drive tissue-preferred gene expression are determined and isolated. Said elements are then inserted control region is linked in cis to a gene encoding an assayable product. Said assayable product may include but is not limited to β-glucuronidase (GUS), luciferase, β-galactosidase, or chloramphenicol transferase (CAT). Said elements responsible for tissue-preferred gene expression are isolated using methods including but not limited to the following procedures. Nucleotide sequence and restriction enzyme maps of said genomic clones which demonstrate hybridization to said cDNA probe are determined. Using restriction enzyme digestion and subcloning methods well known to those skilled in the art, expression vectors are constructed comprising various regions of said genomic clone linked in cis to a gene encoding said assayable product to generate an expression vector in which expression of an assayable product is driven by said various regions of said genomic clone. A further method includes the utilization of an oligonucleotide comprising nucleotide sequence complementary to the 5' region of said transcriptional control region of said gene expressed in a tissue-preferred manner and an oligonucleotide comprising nucleotide sequence complementary to a 3' region of said transcriptional control region of said gene expressed in a tissue-preferred manner are synthesized. Preferably, each oligonucleotide further comprises nucleotide sequence corresponding to a restriction enzyme site compatible for cloning into an expression vector comprising a gene encoding an assayable product. Following amplification of DNA comprising the transcriptional control region, cloning of said region into said expression vector is accomplished using techniques well known in the art. Use of the above-described methodologies results in the construction of expression vectors comprising separate potential transcriptional control regions linked in cis to a gene encoding an assayable gene product.

To confirm that said transcriptional control region functions in a tissue-preferred manner in plant tissues, said expression vector comprising a transcriptional control region of a gene expressed in a tissue-preferred manner in plants linked in cis to an assayable product is transfected into plant cells or tissues. The method utilized for transfection of various types of plant cells or plant tissues may include but is not limited to particle bombardment, liposome-mediated transfection, calcium phosphate-mediated transfection, viral gene transfer, or electroporation. Said various cells or tissues may be transfected in vitro after excision from said plant. Following a defined period of time after transfection of said construct into said tissues, the issues are harvested and an assay capable of detecting said assayable product is performed. The amount of assayable product detected in said cells or tissues is proportional to the ability of said transcriptional control region to function in that cell or tissue. In this manner, the ability of said transcriptional regulatory region to drive tissue-preferred gene expression is determined. Alternatively, said cells or tissues may be transfected and utilized to generate a transgenic plant. Following transfection, said transgenic plant has a copy of said expression vector comprising said transcriptional control region linked in cis to a gene encoding an assayable product incorporated into the genome of the plant. In most cases, said copy is present in each cell and tissue of said transgenic plant. Harvest of said tissues is followed by assay of said tissues for expression of said assayable product. The amount of said assayable product in each of said tissues is determined and is proportional to the level of expression of said gene encoding said assayable product in each of said tissues. In this manner, then, the ability of the transcriptional control region of said cDNA to drive tissue-preferred gene expression is determined.

The ability of a transcriptional control region of a gene to drive expression of a reporter or effector gene in a floral-preferred manner to confer a selective advantage to transformed plants is tested by the generation of a transgenic plant. A transgene comprising a putative floral tissued-preferred transcriptional control region driving expression of effector gene that confer said selective advantage is transfected into a plant cell, tissue or regenerable culture and may be allowed to develop into a plant. Said transgenic plant is then allowed to mature and is challenged by an adverse condition in which those plants expressing the transgene would retain a selective advantage over non-transformed plants. One such advantage may be conferred upon a plant following transfection with a DNA molecule comprising an ear-mold resistance gene such as a peroxidase (Lagrimini, et al., Hortiscience 28:218–221), a chitinase (Broglie, et al. Philos. Trans. R. Soc. Lond. [Biol.] 342:265–270), an anti-fungal peptide (Duvick, et al. J. Biol. Chem. 267:18814–18820) or an enzyme having the ability to detoxify a mycotoxin (Duvick, et al. Fumonisin-detoxifying enzymes, WO 96/06175) operably linked to a floral tissue-preferred transcriptional regulatory region.

Said transcriptional control region may also be utilized to drive expression of genes involved in other aspects of plant physiology including but not limited to resistance to pests other than insects, growth of the plant, resistance of fruits or vegetables to spoiling, or resistance to adverse weather conditions or herbicides. Said pests other than insects include but are not limited to vertebrates such as birds, rabbits or rodents. Said pests other than insects may also include but are not limited to bacteria, parasites, fungi, viral agents, viroids, and prions. The growth characteristics of a plant include but are not limited to those which result in the production of increased amounts of fruit, increased amounts of seed, growth at either a faster or a slower rate, or growth in a season other than that considered ordinary for said plant. Adverse weather conditions to which the plant may become resistant include but are not limited to temperatures above or below that which the plant is not ordinarily able to survive, flooding, and drought.

The following examples illustrate particular embodiments of the present invention and are not limiting of the specification and claims in any way.

EXAMPLE 1

Isolation of Mutant Maize P-rr Alleles

DNA was isolated from young leaves of individual maize plants and RNA was isolated from pericarps peeled from kernels at various stages of development. The plant material was frozen in liquid nitrogen and stored at −70° C. The procedures utilized for DNA and RNA isolation, Southern blot and northern blot were carried out as described by Lechelt et al. (1989). Double strand sequences were determined for the 5' of P-rr gene from position −11,376 bp to the transcription start site. The Ac insertion site was determined by amplifying and sequencing one of AC/P gene junction fragments. The eight nucleotides immediately adjacent to Ac most likely represent the 8-bp duplication typically resulting from Ac insertion. For mapping the 1.6-kb insertion in the first 1.2 SalI repeat, the Primer SL666 (GCCGCCGTTACATTACATTCT in 5' non-repeated region; SEQ ID NO:7) and SL667 (CGTCGTCAGCCTGCCTGG in 3' repeated region; SEQ ID NO:8) was used to amplify genomic DNA from the P-rr-1088-3 allele. PCR conditions for mapping Ac and 1.6-kb insertion were as described by Perking Elmer-Cetus. Reactions were heated at 94° C. for 6 min followed by 30 cycles of 1.5 min at 94° C., 1 min at 94° C., and 1 min at 70° C. followed by a single extension cycle of 20 min at 72° C. Reaction products were analyzed by agarose gel electrophoresis and cloned into T7-Blue PCR vector (Novagen) and the nucleotide sequence of each product determined.

A gene that has been demonstrated to be expressed preferentially in floral tissues of maize is the P gene. The maize P gene affects phlobaphene pigmentation of the pericarp (outer covering of the kernel, a remnant of the ovary wall), cob glumes, and other floral organs. The P-vv allele, expression of which results in variegated pericarp and cob, contains the transposable element Ac inserted into a P-rr allele (Emerson 1917, Brink and Nilan 1952; Lechelt et al. 1989). P-vv is known to have spontaneously mutated to P-ovov, which specifies orange variegated pericarp and cob (Peterson, 1990). Other alleles into which the Ac element has transposed include Prr1088-3, Prr-111:66, P9D47, P9D205B, and P-ovov-Val.

Figure 2:
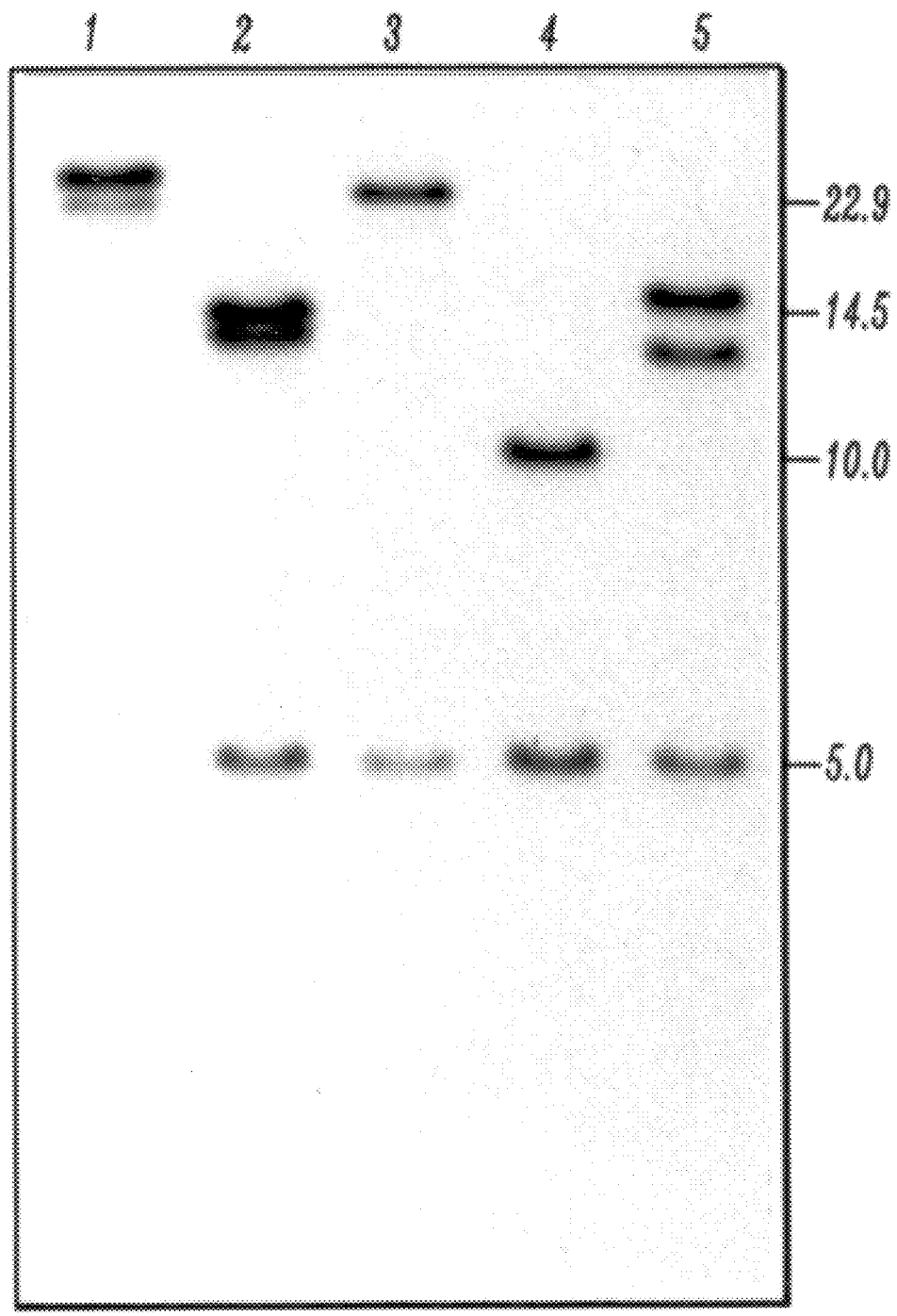
FIG. 2 Southern blot analysis of five P alleles. Genomic leaf DNA was extracted from maize leaf tissue and digested with EcoRI. Southern blotting was then performed using the P-rr-4B2 allele as a probe. Lane 1=P-rr-1088-3, Lane 2=P-vv-1114, Lane 3=P-rr-4B2, Lane 4=P-ww-1112, and Lane 5=P-ovov-1114. The molecular weight (kb) standards are indicated. Integration of the 1.6-kb insertion results in the appearance of a 5 kb EcoRI fragment to all but Prr-1088-3.

The P-rr coding region is flanked by two highly homologous 5.2-kb direct repeats (Athma and Peterson 1991). The downstream 5.2 kb repeat (hatched box in FIG. 1) overlaps two tandem 1.2-kb repeats (dotted boxes in FIG. 1). The upstream 5.2-kb repeat is similarly arranged, except that a 1615 bp insertion within the 5'-most 1.2-kb repeat is present. Sequence analysis revealed the 1615 bp insertion is flanked by 9 bp direct repeats (CCCAGTGAG) and 17 bp inverted repeats (CACGGTTTACAAAACGG; SEQ ID NO:9) and harbors triplets of a 185 bp direct repeat and contains a EcoRI site. FIG. 2 shows a Southern blot of five P alleles. The P-rr-4B2 allele appears to have a single 1615 bp insertion, resulting in the appearance of the additional 5 kb band without the appearance of "additional" upper bands (FIG. 2, lane 3). The P-rr-4B2 allele is designated the "standard" allele for comparison to further alleles comprising the present invention. Compared to the P-rr-4B2 allele (FIG. 2, lane 3), alleles P-vv-1114 (FIG. 2, lane 2) and P-ovov-1114 (FIG. 2, lane 5) have an extra band that has been attributed to Ac insertion and orientation (Peterson, 1990). Allele P-ww-1112 (FIG. 2, lane 4) is the result of a homologous recombination deletion derived from P-vv (Athma and Peterson, 1992). Yet another P-rr allele, P-rr-1088-3 (FIG. 2, lane 1), was isolated and found to lack the 1615 bp insertion and to produce more red pigmentation when compared with standard P-rr-4B2. The 1615 bp insertion introduces one EcoRI site and adds a 5-kb band in each allele (lanes 2 to 5) other than P-rr-1088-3 (lane 1), indicating P-rr-1088-3 (lane 1) might lack this insertion. PCR amplification of DNA from allele P-rr-1088-3 with primers complementary to the flanking regions of the 1615 bp insertion produced a 400 bp fragment as compared to the expected 2-kb fragment. The nucleotide sequence of the 400 bp fragment does not indicate the presence of the 9 bp direct repeat or any portion of 1.6-kb insertion sequence.

Interestingly, the P-rr-1088-3 line produces more red pigmentation than the standard P-rr allele, P-rr-4B2. The allele P-rr-1088-3, which lacks the 1.6-kb insertion, produces darker pigmentation than the standard P-rr-4B2 allele, suggesting that the remaining portion of the 5' 1.2-kb repeat of the upstream 1.2-kb doublet continues to function as an enhancer. It is possible that the 1.6-kb insertion reduces P-rr expression since the insertion might have disrupted the function of the first 1.2-kb repeat. Noticeably, a similar portion of the second 1.2-kb repeat is critical for regulating P-rr expression as defined by Ac mutagenesis (P9D47B and R-165). In summary, both Ac and 1.6-kb insertions revealed the complexity of the P-rr gene promoter.

Moreno et al. (1992) found two upstream regions of the P-rr gene that were sensitive to insertion of the transposable element Activator (Ac). The first site is an approximate 1.3 kb region immediately 5' of the transcription start site (TSS), and the second site is the 1.2-kb SalI fragment located about 5 kb upstream (−6122 to −4853) of the TSS. These two regions are indicated by open triangles in FIG. 1. Ac transposition into either of the two regions was shown to reduce red pigmentation in pericarp. The current invention relates to several independently P-rr alleles comprising various mutations of the P-rr gene promoter related to several events of Ac insertion into at least one of these two regions. The allele P-ovov-Val harbors Ac at position −47 relative to the transcription start site (TSS); its variegated phenotype is shown in FIG. 1. Based on this data, it can be speculated that the TSS-proximal 1.3 kb region contains essential P-rr promoter elements. Ac insertions resulting in the creation of two additional alleles, P9D47B and R65, were mapped to the 1.2-kb SalI fragment, with Ac inserted at positions −5034 and −4960 from the TSS, respectively. The variegated phenotype of the P-9D47B is shown in FIG. 1. The medium variegated pericarp phenotype of R165 was described by Moreno et al. (1992). Clearly, the 1.2-kb SalI fragment appears to play a role in the regulation of P-rr expression, but its actual function remains unclear.

Two further cases of Ac insertion resulting in the formation of new P-rr alleles, P-9D205B and P-rr-11:666, are also included as examples of the present invention. Expression of these alleles does not reduce P-rr expression significantly. As shown in FIG. 1, Ac insertion resulting in the creation of P9D205B and P-rr-11:666 does not reduce pigmentation significantly, indicating that the sequence around these particular Ac insertion sites are not essential for P-rr expression in vivo. The P9D205 allele has Ac inserted in the middle of a 5.2-kb direct repeat, at −2712 bp relative to the P-rr gene TSS. P9D205 was recovered during analysis of twine sectors induced by Ac excision. The P-rr-11:666 allele has Ac inserted at −8813 bp from TSS, ie., in the 3.0-kb SalI fragment upstream of the 5.2-kb direct repeat (FIG. 1). The P-rr-11:666 allele was recovered during analysis to determine the nature of an unstable P-rr allele derived from P-vv (Athma and Peterson, 1992). An Ac insertion in the 3.0-kb SalI fragment that did not result in a variegated phenotype has been reported (Chen et al., 1992). It is possible that additional Ac insertions in these regions may not have been detected if they had little effect on P-rr gene expression. Ac has likely transposed into many sites in the 8.8 kb P-rr promoter, but only insertions within the 1.3 kb or 1.2 kb regions result in distinguishable phenotypes. The insertion in P-rr-11:666 probably defines the maximum length (8813 bp) of the largest plant promoter (Moreno et al., 1992). The phenotype resulting from expression of the P-9D205B allele indicates that some of 5.2-kb repeat sequence is not required for regulation of the P-rr promoter. Another feature of the P9D205 B insertion is that regulation of P-rr expression by the 1.2-kb SalI fragment is distance insensitive, since the 4.6-kb Ac insertion in the middle of 5.2-kb repeat almost doubles the distance of the 1.2-kb fragment from the TSS, having no distinguishable effect on gene expression. This indicates that the 1.2 kb SalI fragment does possess enhancer-like activity. Each Ac insertion studied, including those that have an effect on P-rr expression, as well as those having no effect on P-rr expression, are valuable tools with which the functional elements of the P-rr promoter and this invention have been defined.

In order to understand the evolution of the P-rr gene promoter, the origin of the 5.2-kb direct repeats must be defined. A Tourist-like mobile element (Bureau & Wessler, 1992) has been previously identified in the 5' region (around the HindIII site near the TSS, see FIG. 3) of the P-rr gene. Both copies of the 5.2 kb direct repeats, which flank the P-rr gene, contains same element at identical sites. This suggests that insertion of the Tourist-like element occurred prior to a duplication of the 5.2 kb direct repeats flanking P-rr. This line of evidence suggests that the 5.2 kb direct repeats may result from duplication. Interestingly, this Tourist element is also present in the B-I promoter (Radicella et al., 1992).

The overall structure of the P-rr gene is similar to the structure of a retrotransposon, although there were not any evidence to support the mobility of P-rr gene. The following structural features of the P-rr gene support our hypothesis that the P-rr gene may represent a primitive retrovirus or retrotransposon. First, two inward-oriented tRNA repeats 303 to −409 and −987 to −897) are present within the P-rr promoter. In retrotransposon, tRNA is known to serve as a replication primer (Bingham and Zachar, 1989). It is currently unclear as to which RNA polymerase (II vs. III) transcribes the P gene. In some instances, RNA polymerase III has been shown to transcribe tRNA genes normally transcribed by RNA polymerase II (Carlson and Ross, 1983). Our results indicate that the tRNA-containing region functions as an enhancer in regulating P-rr expression. Further retrotransposon-like structural and functional features of the P-rr promoter include the function of the 5' 1.2-kb doublet as an enhancer which resembles the function of the U3 element in the retrovirus. This doublet of 1.2 kb repeats is also present in the 3' region of the P-rr gene, similar to the UP elements of retrovirus (Bingham & Zachar, 1989). Additionally, sequences with high identity to retrotransposon sequences the further 5' region of the P gene are observed. Computer-assisted analysis indicates that three regions of the 5' start site of the P-rr gene demonstrate a significant degree of identity with retrotransposon genes. The region comprising −10348 to −10193 indicates 63.2% identity to the *Brassica napus copia*-like retrotransposon reverse transcriptase (Voytas et al., 1992. The region comprising −10344 to −10070 is 61.7% identical to the *Ginkgo biloba copia*-like retrotransposon reverse transcriptase gene (Voytas et al., 1992). The region comprising −10557 to −9843 is 51.4% identical to the *Arabidopsis thaliana* (Kashir) retrotransposon Tal-2 DNA (Konieczny et al., 1991). The early observation of a smear of RNA suggested that this region contains repetitive DNA sequences which demonstrate similarity to a range of transcripts of various sizes (Lechelt et al., 1989). However, reconstruction of the complete retrotransposon structure in the 5' region of P-rr has not been possible and may be due to re-arrangement that occurred after retrotransposon insertion.

EXAMPLE 2

Construction of Floral Tissue-Preferred Expression Vectors

In order to generate plasmid vectors for use in driving floral tissue-preferred gene expression in maize, several constructs were engineered and tested in plant cells derived from floral and non-floral maize tissues. A BamHI site was introduced 5' to the ATG codon by site-directed mutagenesis (Su & El-Gewley, 1998) of the fragment comprising the maize P-rr gene promoter (−1252 to −1) and untranslated leader (0 to +325; Grotewald, 1991). This fragment was then fused to the 5' BamHI site of the 1870-bp fragment containing the b-glucuronidase (GUS) coding region (Jefferson et al., 1986). Pb::GUS was derived from P1.0b::GUS by deletion of 1017 bp (P1.0 fragment from HindIII to SalI) and served as the basal construct containing a TATA-like box (located at position −33). The 1.0-kb region (P1.0 ) immediately adjacent to the basal region (Pb) contains two tRNA domains (−303 to −409 and −987 to −897) and three copies of SV40 virus enhancer consensus sequence (Weither et al., 1983). The distal 1.2-kb SalI fragment (P1.2) was ligated to the Pb fragment at the SalI site to construct the P1.2b::GUS expression. The P0::GUS construct does not contain any P-rr promoter sequences, but the GUS gene alone. In addition, the above-described plasmids include the potato pinII terminator sequences (An et al., 1989) and a BamHI fragment containing the 579 bp maize AdhI-S intron I (Dennis et al., 1984) inserted at the BamnHI site between the promoter and the GUS gene. Plasmid SL100 (PHP5963) is essentially identical to P1.0b::GUS (PHP5955) with the difference being the absence of the AdhI-S intron 1. Plasmids SL101, SL102, and SL103 were constructed from the P-rr promoter HindIII fragments −1253 to −2255, −3616 to −2254, and −3617 to −6411, respectively. Each individual region was isolated from plasmid PA101 and ligated into SL100 5' to the Pb promoter fragment. Reporter constructs include PHP687 comprising a 35SCaMV promoter driving expression of the Cl and R anthocyanin genes (Bowen, 1992), PHP1528 comprising the 35SCaMV promoter driving expression of Luciferase (Dewet et al. 1987. Mol. Cell. Biol. 7: 725–737), and plasmid PHP3528 comprising the 35SCaMV promoter driving expression of the Bar gene (Block et al., 1987). All three constructs contain a AdhI-S intron and potato pinII terminator.

Maize suspension cells (endosperm cell cultures derived from inbred line A636, BMS cells derived from the Black Mexican Sweet stem cells, and embryogenic cells derived from a cross of inbred lines W23×B73) have been described by Linger et al., (1993) as well as Grotewold et al., (1994). Bombardment conditions and transient expression assays for luciferase and GUS were performed essentially as previously described (Klein et al., 1989; Bowen, 1992). For each bombardment, 100 mg of cells was placed on filter paper premoistened with 1 ml of growth medium. Cells were harvested 4 to 5 days after subculture and, prior to bombardment, treated overnight in growth medium containing 0.25M mannitol. Preparation of protein extracts from the bombarded cells and the subsequent GUS assay were essentially as described by Linger et al. (1993). The GUS-light protocol (Tropix, Inc.) was also utilized for the experiments related to stable callus lines and plants.

Ears from the maize High Type II line were harvested 15 to 20 days after pollination (DAP). Kernels were removed from the ear and placed on a solid medium and bombarded immediately. The kernels were exposed to light to induce the anthocyanin formation for two days (Bowen, 1992) and photographed for those with red sectors, then, stained for GUS expression in a solution containing 5-bromo-4-chloro-3-indolyl glucuronide (X-gluc) and incubated at 37° C. for 48 hours.

Figure 3:
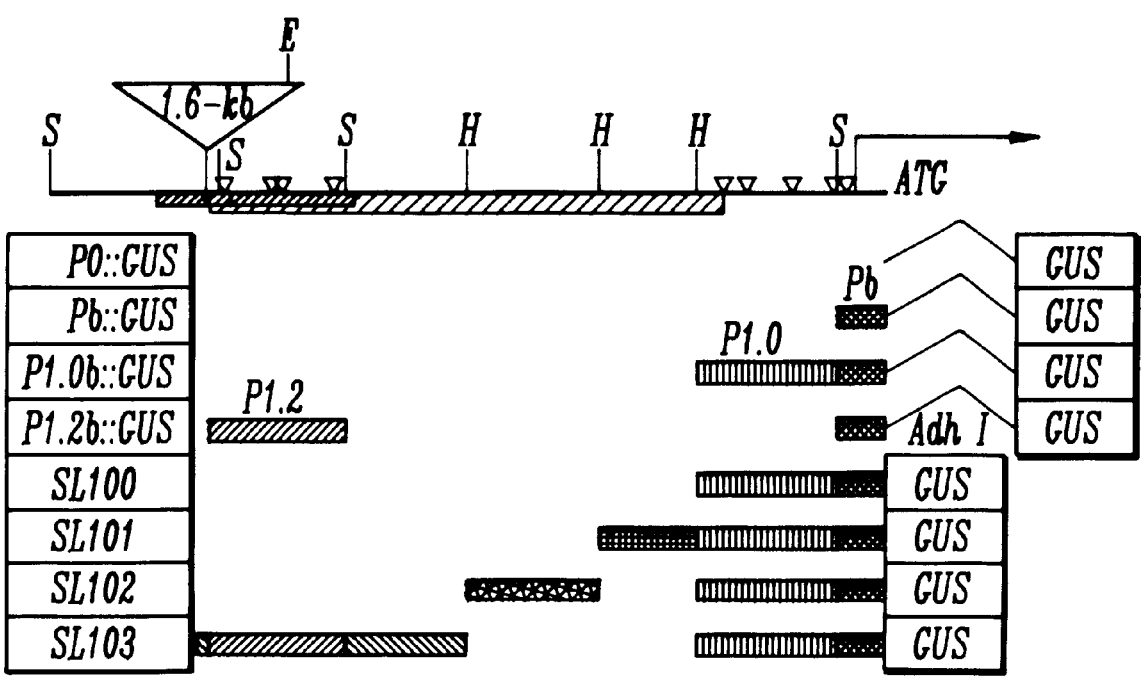
FIG. 3 P::GUS constructs. Eight separate b-glucuronidase (GUS) gene constructs comprising the indicated regions of the P gene promoter operably linked to the GUS reporter gene are indicated. The Adh1 intron in P0::GUS, Pb::GUS, Pb1.0::GUS and Pb1.2::GUS is indicated and is not present within SL100, SL101, SL102, or SL103.

In order to determine the activity of the various P-rr promoter expression vectors in maize, the activity of the cloned P-rr promoter fragments were analyzed in transient assays. The basal plasmid, Pb::GUS contains the maize AdhI-S intron and GUS gene under control of the 559 bp Pb promoter fragment (326 bp untranslated leader and 233 bp immediately 5' of the transcription start site). The promoter fragments of other test plasmids P1.0b::GUS (PHP5955) and P1.2b::GUS consist of the Pb and the 5' adjacent 1.0 kb (P1.0 ) or the upstream 1.2 kb SalI fragment (P1.2), respectively (FIG. 3). Plasmid SL100 (PHP5963) is essentially identical to the P1.0b:GUS (PHP5955) except the AdhI intron has not been incorporated into this construct. Additional fragments, −1253 to −2255 (SEQ ID NO: 4), −2256 to −3617 (SEQ ID NO: 5), and −3617 to −6411 (SEQ ID NO: 6) were ligated into SL100 to construct SL101, SL102, and SL103 respectively (FIG. 3). As described for the SL100 plasmid, these constructs do not include the AdhI intron.

Expression vectors (Pb::GUS, P1.0b::GUS, and P1.2b::GUS) comprising specific regions of the P-rr promoter (SEQ ID NO: 1, SEQ ID NO: 2, and SEQ ID NO: 3, respectively) were introduced into the separate groups of suspension cells (endosperm cell cultures derived from inbred line A636, BMS cells derived from the Black Mexican Sweet stem cells, and embryogenic cells derived from a cross of inbred lines W23×B73) using a biolistic particle accelerator to determine the levels of gene expression directed by each individual promoter region. Test plasmids were co-bombarded with a reference plasmid, PHP1528 (35S::Luciferase), into each of the three types of above-listed suspension cells. The reference plasmid (PHP1528) comprises the coding sequence of the firefly luciferase gene fused to the cauliflower mosaic virus (CAMV) (53S) promoter and serves as an internal control for bombardment and normalization. GUS activity was detected in extracts of cells transformed with the three constructs containing AdhI intron (Pb::GUS, P1.0b::GUS, and P1.2b::GUS). GUS activity in cell extracts of cells transformed with each of the four plasmids without AdhI intron (SL100, SL101, SL102, SL103) was too low to be detected.

Figure 4A:
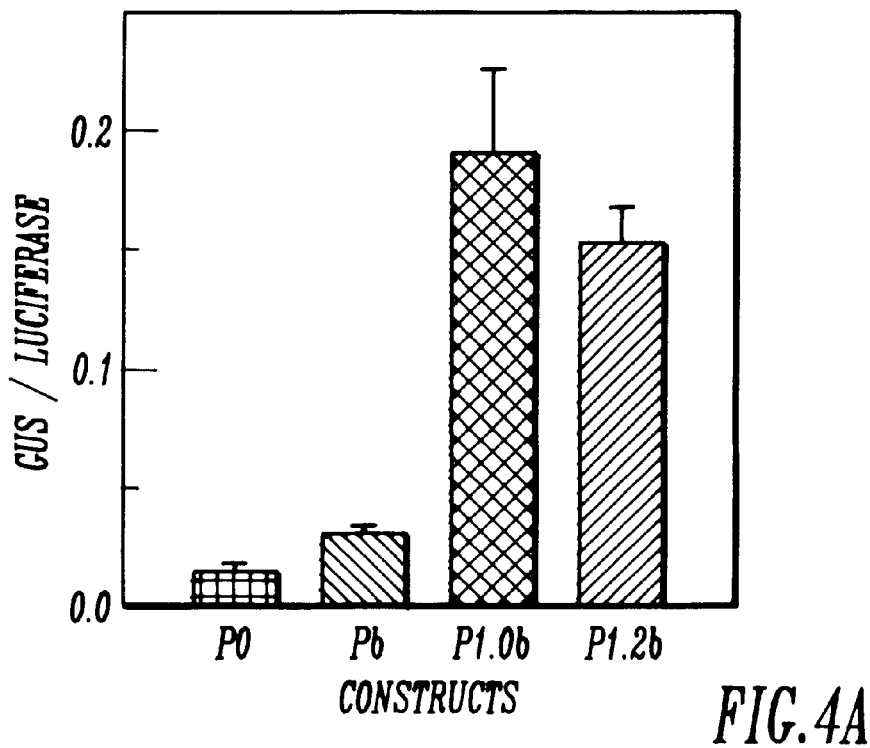
FIGS. 4A–B Activity of the P gene promoter reporter constructs in BMS cells (4A) and pericarp (4B). Cells were co-transfected with an additional reporter construct in which the luciferase gene is under control of the CaMV 35S promoter. GUS activity has been normalized to luciferase activity. The P0, Pb, P1.0b, and P1.2b are designated P0::GUS, Pb::GUS, P1.0b::GUS, and P1.2b::GUS, respectively.
Figure 4B:
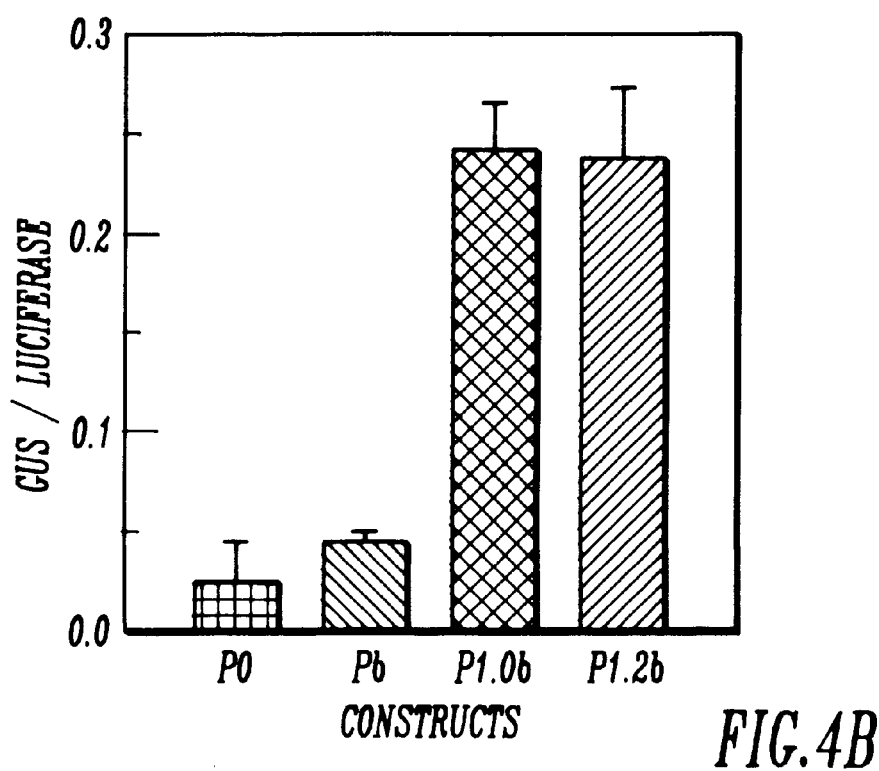

Expression vectors Pb::GUS, P1.0b::GUS and P1.2b::GUS were co-bombarded with the 53S::Luciferase into maize BMS cells and the normalized GUS activity is shown in FIG. 4A. Construct P1.0b::GUS and P1.2b::GUS gave 10.4 and 8.2 fold increase in GUS activity, respectively, relative to GUS expression from basal construct (Pb::GUS). Therefore, the P1.0 and P1.2 sequences demonstrate enhancer-like activity in BMS suspension cells. Pericarps were also transformed by bombardment to compare the GUS activity of the three plasmids in this cell type. Similar to the results from suspension cells, the activities of P1.0b::GUS and P1.2b::GUS in pericarps were significantly higher than that of Pb::GUS (FIG. 4B).

Figure 5A:
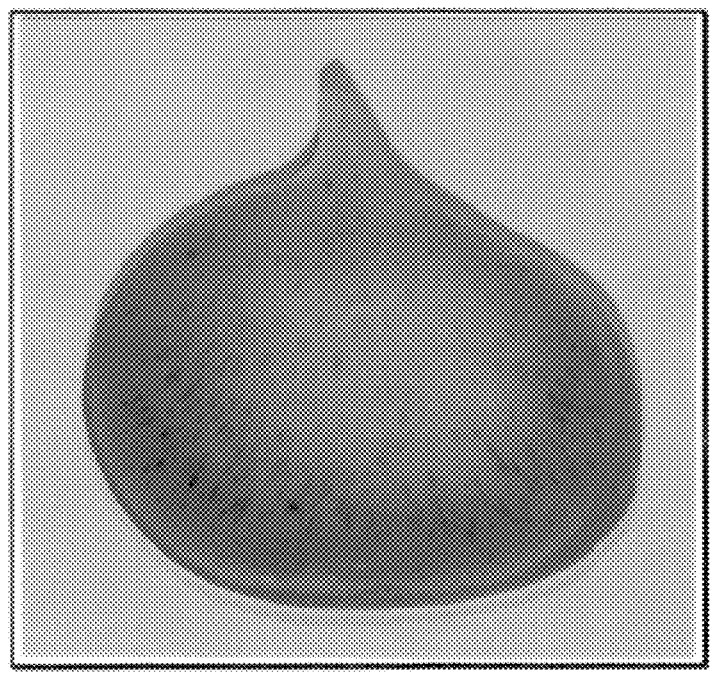
FIGS. 5–F Response of kernel pericarps to bombardment with plasmids Pb::GUS, P1.0b::GUS, and P1.2b::GUS. Kernel pericarps presented in panels A, C, and E expressing anthocyanin sector (from 35S:: C+R) before GUS staining are identical to those pericarps expressing the GUS gene as indicated in panels B, C and F representing PB::GUS, P1.0b::GUS, and P1.2b::GUS, respectively. Pericarp material was between 15 to 20 days after pollination (DAP). After co-bombardment, the kernels were exposed to light for two days to express Cl+R genes, e.g., red anthocyanins sector (Lugwig et al., 1990) and photographed. Then, the same kernel was stained with X-Gluc to reveal GUS expression. Therefore, the expression of the R+C genes and the GUS gene were compared in the same kernel. Transformation with either P1.2b::GUS (D) or P1.0b::GUS (F) results in the isolation of a greater number of blue loci than the PB::GUS (B), although the pericarp bombarded with PB::GUS (A) reveal a greater number of red sectors than that of C and E.
Figure 5B:
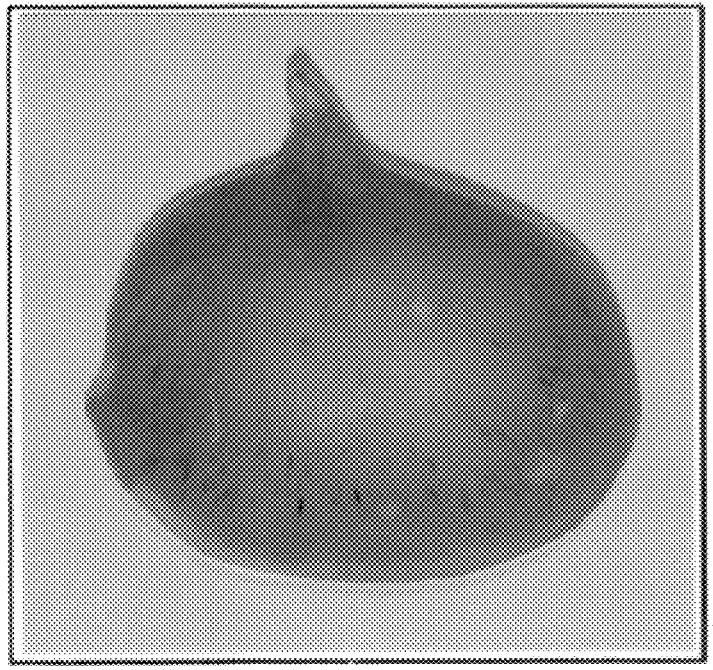
Figure 5C:
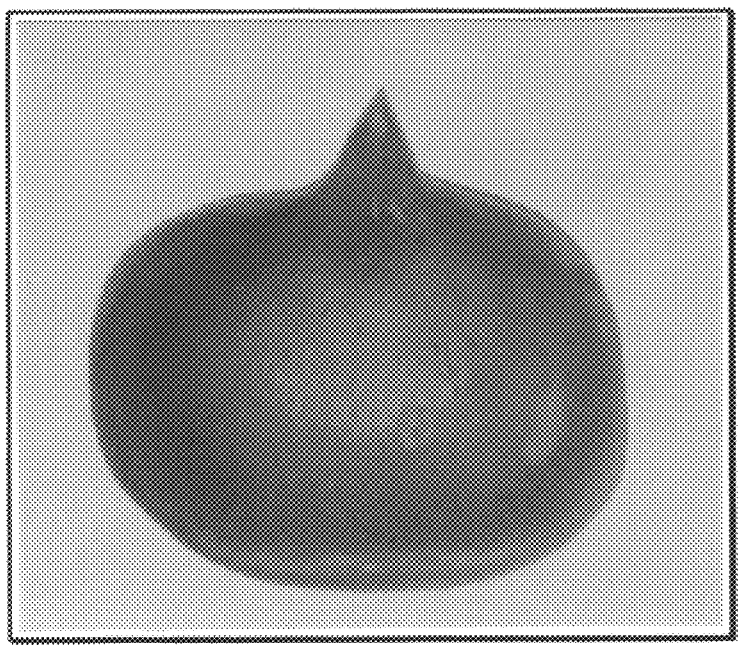

Visualization of bombarded kernels further supports the above-described results. The kernels showing red anthocyanin sectors before GUS staining in FIGS. 5A, 5C, & 5E are identical to kernels shown after GUS staining demonstrated in FIGS. 5B, 5D, & 5F. Noticeably, some red sectors bleached out during GUS staining. The kernels bombarded with P1.0b::GUS (FIG. 5D) and P1.2b::GUS (FIG. 5F) demonstrate greater intensity of GUS staining than that of PB::GUS (FIG. 5B) indicating that both P1.0 and P1.2 fragments enhance the Pb activity. This enhancement is not due to bombardment variation because more red sectors in the kernel of FIG. 5A than those of FIG. 5C and FIG. 5E indicate the kernel of FIG. 5A received more bombarded particles than that of FIGS. 5C and 5E. Hence, P1.0 and P1.2 also function as enhancers in intact pericarps.

Figure 7:
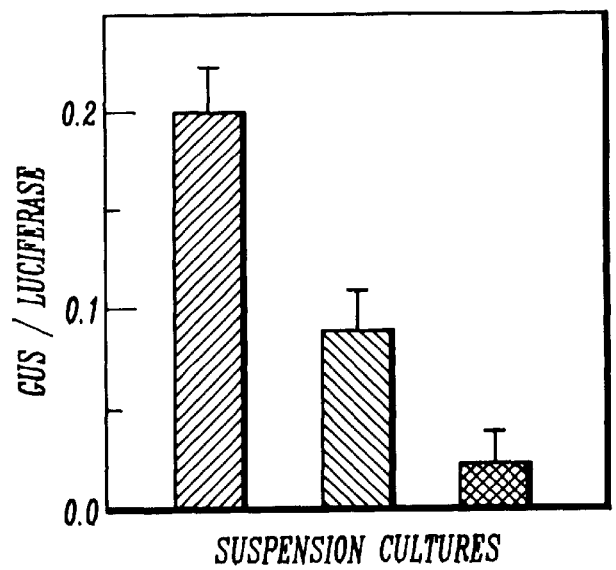
FIG. 7 Response of Black Mexican Sweet suspension cells (left-hand column), endosperm-derived suspension cells (center column) and embryogenic culture suspension cells (right-hand column) to bombardment with P1.0b::GUS. GUS activity was normalized to luciferase activity by co-transfection with the 35S::Luciferase vector.

It was particularly important to determine the level of gene expression driven by the cloned fragments of the P-rr promoter in endosperm. It is considered important by those skilled in the art to utilize the P-rr promoter to direct expression of ear-mold resistance genes in pericarps with very low levels of leakage into endosperm. Suspension cells were derived from maize endosperm, Black Mexican Sweet corn (BMS) stem cells (Linger et al, 1993), and embryos of inbred lines W23×B73 (Grotewold et al., 1994). The P1.0b promoter gave high, moderate, and low levels of GUS activity in BMS cells, embryogenic suspension cells, and endosperm suspension cells, respectively (FIG. 7). Similar results were visualized using a reference plasmid (PHP687) that expresses genes for the production of red anthocyanin pigments, as a control for bombardment efficiency. The ratio of blue vs. red cells was higher in BMS and embryogenic suspension cells and lower in endosperm-derived suspension cells (data not shown). Low activity in endosperm-derived suspension cells indicates that tissue-specific gene expression driven from the P1.0b fragment is similar to the tissue-specific expression of P-rr observed in planta since endogenous P-rr mRNA is not detectable in endosperm (Grotewold et al., 1991). The P1.2b::GUS also demonstrated a similar pattern of expression to the P1.0b::GUS in three types of suspension cells. The activity of the basal plasmid (Pb::GUS) was much lower (data not shown). The cloned P-rr promoter fragments demonstrated relatively low expression in endosperm-derived suspension cultures.

Figure 8:
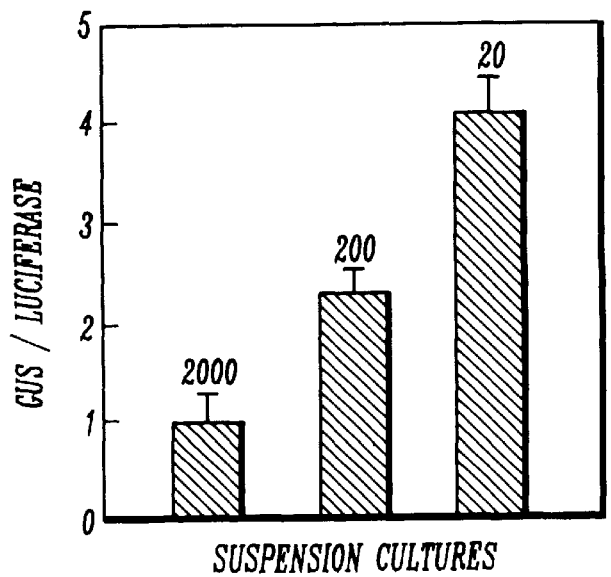
FIG. 8 Effect of DNA dosage on P1.0b::GUS expression in pericarp and scutellum. Lane 1 (proximal to the Y-axis) represents activity following transfection with 2000 ng P1.0b::GUS/transfection. Lane 2 (middle column) represents 200 ng P1.0::GUS/transfection. Lane 3 (distal to the Y-axis) represents 20 ng P1.0::GUS/transfection. GUS expression (GUS/Luciferase) was compared between pericarp and scutellum and is presented as a numerical value representing the pericarp/scutellum ratio along the Y-axis.

In order to further study gene expression controlled by the Pb, P1.0b and P1.2b promoter fragments, pericarps and scutellum were transformed with the expression plasmids Pb::GUS, P1.0b::GUS or P1.2b::GUS. Neither P-rr mRNA (Grotewold et al., 1992) nor pigmentation is detected in scutellum, indicating that the P-rr gene is not expressed in this tissue. Preferential expression in pericarp vs. scutellum would indicate that the cloned P1.0b promoter fragment harbors the floral specific elements. A variable amount of P1.0b::GUS DNA was co-bombarded with the reference plasmid PHP1528 (53S::Luciferase) into scutellum and pericarp. The PHP1528 was kept at constant concentration, 2 mg per bombardment. An inverse relationship between the amount of DNA transfected and preferential expression in pericarps. At high DNA doses (2 mg P1.0b::GUS per bombardment), expression in pericarp and scutellum was equivalent (FIG. 8). However, decreasing doses of DNA (200 ng and 20 ng of P1.0b::GUS per bombardment)led to increasingly preferential expression in pericarps vs. scutellum (FIG. 8). A similar dose effect on tissue-preferential expression was also observed using reference plasmid PHP687 (comprising 53S operably linked to the Cl+R gene). GUS expression under control of P1.0b fragment in pericarps vs. scutellum increased from 1.7 to 6.2 to 11.1 when the amount of P1.0b::GUS construct was decreased from 2, to 0.2, to 0.02 mg per bombardment, respectively. The results from these transient assays suggests that the P1.0b is expressed preferentially in pericarp.

The importance of the 1.2 kb repeated region (P1.2) has been illustrated by Das and Messing (1994) in studies comparing P-pr and P-rr. Methylation of the P gene was increased in P-pr relative to P-rr, including methylation of the 1.2 kb region. Interestingly, one of two repressed sites of DNase I-sensitivity assay for P-pr was linked to the left SalI site in this 1.2-kb SalI fragment (Lund et al., 1995). However, there are at least three possible explanations for the role of the 1.2 kb SalI fragment, proposed by Moreno et al., (1992). First, the region may contain untranscribed regulatory sequences of P gene. Second, transcription of the P gene may begin further 5' of the cloned region, and the upstream region including P1.2 fragment is actually part of a large intron. Third, the region surrounding P1.2 may be part of an additional separate transcriptional unit which is required for P expression. Our data directly support the first hypothesis that the 1.2-kb SalI fragment functions as an enhancer and do not support the second or the third hypothesis. The coding region of the P gene, positioned 7 kb downstream from the P1.2 fragment, not only activated the Al expression in vitro assay (Grotewold et al., 1994), but produced the compounds of flavan-4-ol in BMS cells when driven by the 35S promoter (Bowen, personal communication). Further, Ac insertion in the allele P-9D205 does not significantly reduce P-rr pigmentation, indicating the particular Ac insertion within this allele comprises DNA sequence that is not essential for P-rr function. Further, the 9D47B allele produces less P-rr mRNA than standard P-rr-4B2 (data not shown), suggesting that the Ac insertion in the 1.2-kb SalI fragment directly regulates P-rr expression.

EXAMPLE 3

Floral Tissue-Specific Gene Expression in Transgenic Maize

In transient assays, the P1.0b::GUS is preferentially expressed in pericarp to scutellum when the amount of DNA was lowered from 2000 to 20 ng per bombardment. Plants transformed with P1.0b::GUS exhibited GUS activity in tissues where endogenous P-rr is expressed, such as pericarps, cob glumes, silks, and husks. GUS activity was not observed in endosperm and embryos organs where P-rr is not expressed. Therefore, the 1.3 kb region immediately upstream of the transcription start site (TSS) contains the elements that determine the floral specificity of P-rr. The High Type II line derived from the cross between B73 and A188 was used in stable transformation. Immature embryos (10–15 DAP), ranging in size from 1.0 to 1.3 mm, were induced to initiate callus for 4 days on N6-based medium. Either cultured immature embryos or callus were transferred to high sucrose medium (6% sucrose) for four hours before bombardment. After bombardment with PDS-1000/HE Biolistic Delivery System (Du Pont) Helium gun, the materials were transferred back to callus induction medium for 4 to 6 days. Stably transformed callus was selected on 3 mg/L bialaphos for 6 to 8 weeks. The bombarded callus material was transferred every two weeks into fresh medium. Transgenic calli were obvious by an accelerated growth rate and size at this stage. Putative transgenic calli were transferred onto fresh selective plates. Individual callus lines were maintained on selective media to increase the amount of material available for initiation of large-scale regeneration efforts. Selective pressure was maintained during the regeneration process (Fromm, 1994).

The region required for floral-tissue specific expression was further defined after analysis of plants stably transformed with Pb::GUS, which contains the 326 bp untranslated leader and 233 bp immediately 5' of the transcription start site. Plants transformed with Pb::GUS demonstrated the pattern of floral tissue-specificity similar to plants transformed with P1.0b::GUS. However, the number of plants (transformed with Pb::GUS) positive to X-Gluc staining was relatively low. This data indicates that the Pb fragment comprises the factors necessary to maintenance of tissue-specific expression. One explanation is that the activity of basal promoter is too low to induce consistently detectable expression in stable transgenic maize. The fact that transgenic plants transformed with P1.2b::GUS demonstrate the identical pattern of tissue-specificity as P1.0b::GUS further supports the idea that the Pb fragment contains the tissue-specific determinants of P-rr expression.

Figure 6:
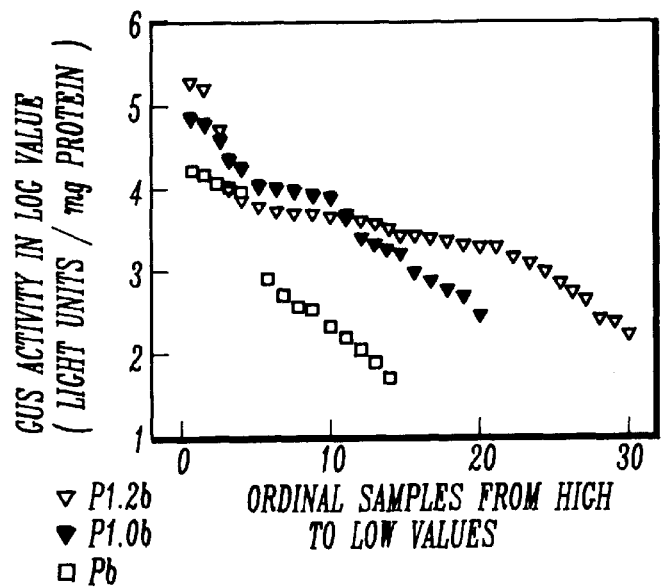
FIG. 6 GUS activity in stable transgenic callus lines. GUS activity was assayed according the GUS-Light protocol (Tropix, Inc., Bedford, Mass.) and is expressed on the Y-axis in log value (light units per mg protein). The X-axis indicates the number of events characterized as high level expression (proximal to the Y-axis), intermediate expression, or low expression (distal to the Y-axis). Data was plotted for P1.0b:GUS (open triangles), P1.2b::GUS (filled triangles), and PB::GUS (open squares), respectively.

The tissue-specific pattern of P::GUS expression, dominant in the female organs including but not limited to silk, pericarp, husk and cob tissues and during late-stage development, suggests that the cloned P-rr promoter fragment may be useful for directing expression of foreign genes for pathogen resistance, such as ear-mold resistance genes, specifically in pericarps, silks, and cob glumes. Transgenic callus events and plants transformed with Pb::GUS, P1.0b::GUS, or P1.2b::GUS were generated to compare the activity of the enhancer-like regions in planta. Four independent GUS assays were performed for each of nine stable callus transformants and the data was ranked from high to low values respectively for Pb::GUS, P1.0b::GUS, and P1.2b::GUS (FIG. 6). GUS expression under control of either P1.0b or P1.2b was higher than that of Pb in stable callus lines. Remarkably, 76% and 54% of the plants transformed with P1.0b::GUS or P1.2b::GUS, respectively, demonstrate GUS-positive staining, in contrast to only 18% of transgenic PB::GUS plants (FIG. 12). In conclusion, the P1.0 and P1.2 fragments not only enhanced Pb activity in the transient assays but also increased Pb activity in stable callus lines and stable transgenic maize plants. Transformation of maize with constructs absent the AdhI intron did not produce any detectable signal in stable callus lines. Furthermore, said constructs produced few GUS-positive plants (FIG. 12). The importance of AdhI intron in boosting gene expression has been previously described in maize protoplast system (Gallie et al., 1994).

Figure 9A:
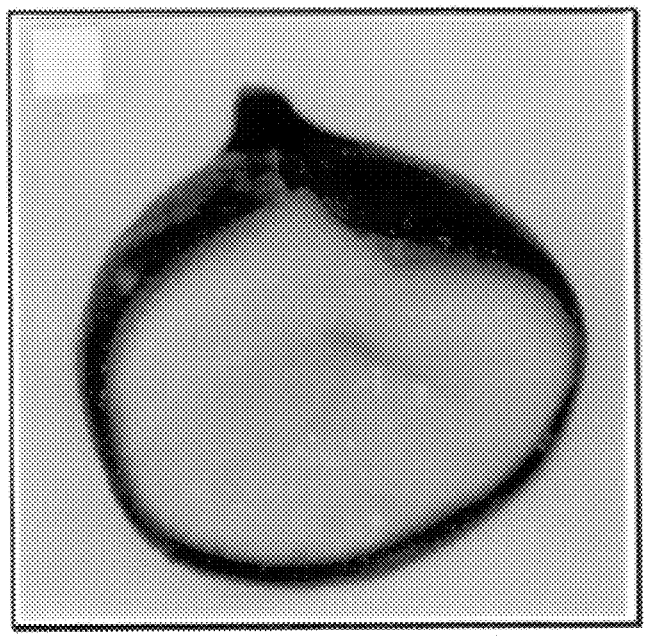
FIGS. 9A–E Floral tissue-preferred gene expression in P1.0b::GUS transformed stable transgenic plants. Transgenic maize stably transformed with P1.0b::GUS were stained for GUS activity in various tissues. A) Expression of the GUS gene specifically in pericarp and lack of GUS expression in the endosperm of a longitudinal section of a 20 DAP kernel. B) Transgenic husks (left) vs. non-transgenic husk (right) at 0 DAP. C) The silks from the transgenic plants. D) GUS expression in pericarps and glumes, and lack of expression in endosperm, embryo, and the pedicel area. E) GUS activity in anthers from transgenic plants (left) vs. non-transgenic plants (right).
Figure 9B:
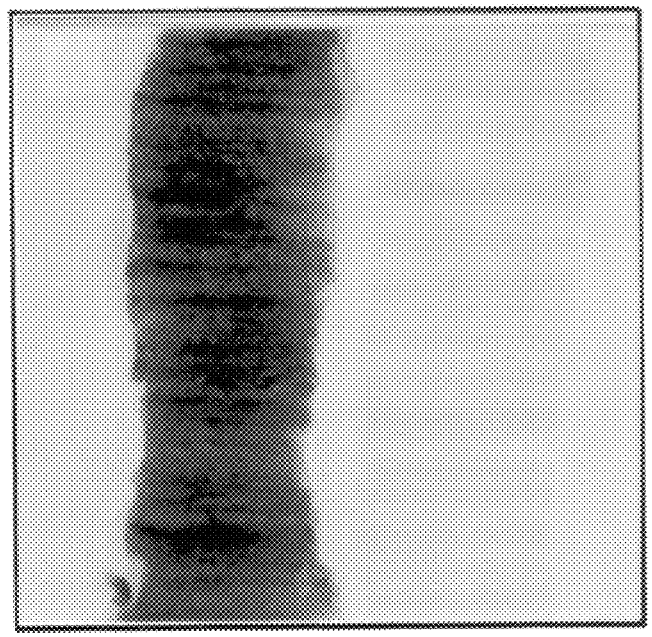
Figure 9C:
Figure 9D:
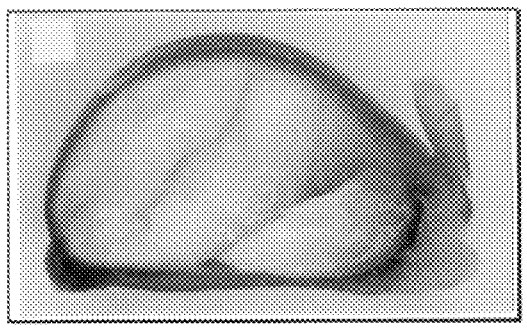
Figure 9E:
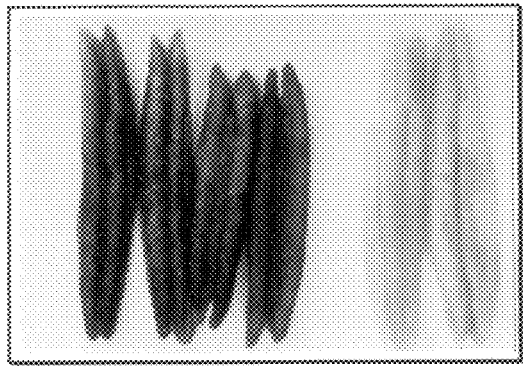

The cloned promoter fragments were expressed in a tissue-specific pattern similar to that of the wild-type P-rr gene, and these were further studied in vivo. The temporal and spatial distribution of the P1.0b::GUS expression was then investigated in stable transgenic maize plants. From 15 stable transformation events, 160 plants transformed with plasmid P1.0b::GUS were produced (FIG. 12). Although GUS activity varied, most of the transgenic corn plants exhibited a distinct floral specific pattern of GUS expression. Floral organs expressing GUS included pericarps (FIG. 9A), husks (FIG. 9B), and silks (FIG. 9C). There was no detectable GUS activity in the endosperm (FIG. 9A), the embryo (FIG. 9D), or the pedicel area (9D). In addition, some transgenic plants exhibited blue anthers (FIG. 9E) and tassel spikelet (not shown). Transgenic plants had no detectable GUS expression in roots and stems. Transgenic plants from one transformation event revealed blue staining in the leaves, but not in floral tissues. However, the majority of transgenic plants demonstrated a floral specific pattern of expression similar to that specified by the P-rr gene and the pattern of P-rr mRNA distribution (Grotewold et al., 1992). Thus, the P1.0b fragment contains the elements sufficient for floral-specific expression of the P-rr gene.

Figure 10:
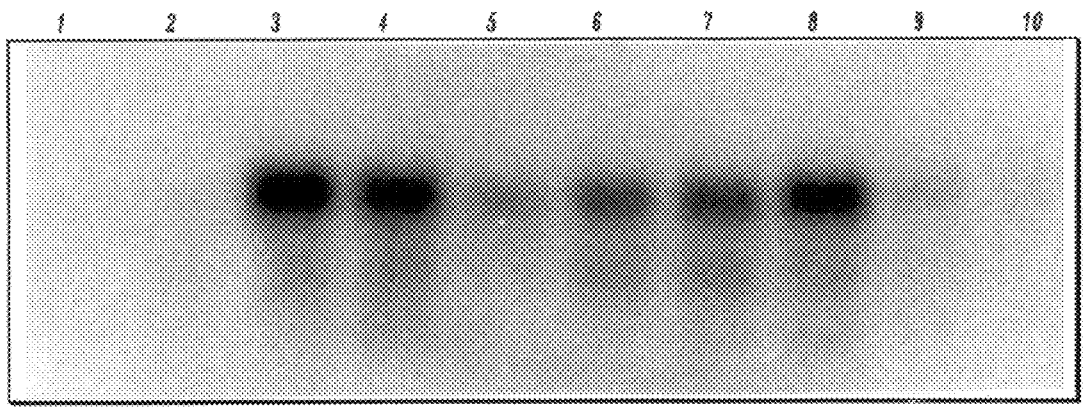
FIG. 10 Developmental profile of P-rr-4B2 mRNA expression. Lane 1=whole ear at 0 DAP, Lane 2=outer ear at 2 DAP, Lane 3=outer ear at 4 DAP, Lane 4=outer ear at 6 DAP, Lane 5=ovules at 8 DAP, Lanes 6, 7, 8, 9, 10 represent pericarps at 12, 16, 20, 24, and 28 DAP, respectively.

There is a significant time delay between expression of P-rr mRNA and the appearance of red pigment specified by P-rr. The Northern blot indicates the P-rr message detectable in ear tissues at four and six DAP (lanes 3 and 4 in FIG. 10). It increases from the 8 DAP to 20 DAP (Lanes 5, 6, 7, 8 in FIG. 10), then, decreases after 20 DAP. The increased signal strength in lanes 3 and 4 as compared to lanes 5, 6, and 7 (FIG. 10) may be due to the inclusion of cob glumes, which express P-rr at a relatively early stage. In contrast to the mRNA profile, the red phlobaphene pigment is usually not observed until 20 days after pollination. This is most likely due to the requirement of physiological maturation for the final polymerization step in the phlobaphene synthetic pathway, as proposed by Styles & Ceska, 1981.

Figure 11A:
FIG. 11 Developmental profiles of the P1.0b driven gene-expression in transgenic maize kernels. Panel A illustrates the GUS expression in glumes and the crown region of pericarp at 0 DAP. Panels C, D, and E demonstrate P1.0b-driven GUS expression in kernels at 20, 25, and 30 DAP, respectively.
Figure 11B:
Figure 11C:
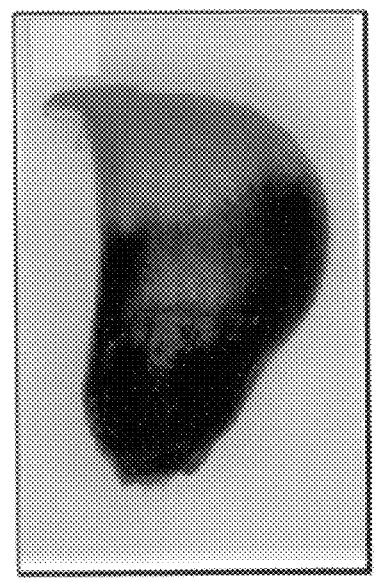
Figure 11D:
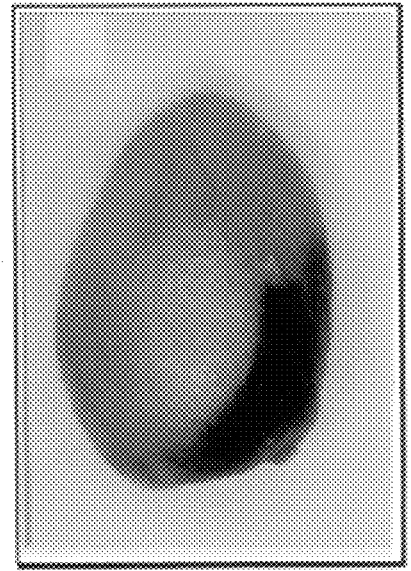

To further confirm the time delay between the accumulation of P-rr mRNA and appearance of P-rr specified-red phlobaphene pigment, expression of P1.0b::GUS was observed for the kernels after pollination. At 0–4 days after pollination (DAP), GUS expression was usually high in glumes and the pericarp crown region (FIG. 11A). As the kernel developed, blue staining intensified toward the middle of the pericarp gown and peaked at 20 DAP (FIG. 11B). As the kernel matured, the GUS coloration started to disappear at the crown region at 25 DAP (FIG. 11C) and decreased further toward the pedicel region at 30 DAP (FIG. 11D). Finally, GUS staining completely disappeared when the kernel were fully mature. The overall developmental profiles of the P1.0b::GUS matches endogenous P-rr mRNA accumulation. The 5' 1.2-kb SalI fragment (P1.2) has been demonstrated to function as an enhancer using in vitro suspension cells and bombarded pericarps as well as in vivo using transgenic callus and plants. The distance insensitivity of the P1.2 enhancer has also been demonstrated in vivo. Insertion of a 4.6 kb Ac element in the middle of 5.2 direct repeat (P-9D205B) did not disrupt P-rr expression.

EXAMPLE 4

P1.0b::Effector Gene Transgenic Plants

The present invention may also be utilized to confer a selective advantage upon a plant. An example includes delivery of a ear mold resistance gene under the transcriptional control of a floral tissue preferred transcriptional control region. An example of such an expression vector comprises a transgene comprising the P1.0b transcriptional control region operably linked to a peroxidase gene. Said expression vector is transfected into a callus culture of maize. A second vector comprising a selectable marker may also be transfected into said callus culture to provide a method for selection of a transformed cell. Transformation and isolation of a transformed cell comprising expansion and growth into a transgenic plant is performed. Following identification of a transformed plant harboring said transgene, said plant is challenged by exposure to an organism that causes ear mold. A plant expressing said ear mold resistance gene is resistant to challenge by said pathogen that causes ear mold. Thus, said floral-tissue preferred transcriptional regulatory element provides a tool with which floral-preferred gene expression of an effector gene confers a selective advantage upon a plant.

While a preferred form of the invention has been shown in the drawings and described, since variations in the preferred form will be apparent to those skilled in the art, the invention should not be construed as limited to the preferred form shown and described, but instead is as set forth in the claims.

REFERENCES

An, G., Mitra, A., Choi, H. K., Costa, M. A., An, K., Thornburg, R. W., and Ryan, C. A. (1989). *Functional analysis of the 3' control region of the potato wound-inducible proteinase inhibitor 11 gene.* Plant Cell 1, 115–122.

An, W. and Wensink, P. C. (1995) *Three protein binding sites form an enhancer eeneser that regulates sex-and fat body-specific transcrition of Drosophila yolk protein genes.* The EMBO Journal 74 (6), 1221–1230.

Atlma, P., Grotewold, E. and Peterson T. (1992). *Insertional mutagenesis of the maize P gene by intragenic transposition of Ac.* Genetics 131:199–209.

Athma, P. and Peterson, T. (1991) *Ac induces homologous recombination at the maize P locus.* Genetics 128, 163–173.

Bingham, P. M. and Zachar, Z., (1989) *Retrotransposon and the FB transposon from Drosophila melanozaster.* In Berg, D. E. and Howe, M. M. (eds.) Mobile DNA, American Society for Microbiology. pp 485–502.

Brink, R. A. and Nilan, R. A. (1952) *The relation between light variegated and medium variegated pericarp in maize.* Genetics 37:519–544.

Benfey, P. N., and Chua, N.-H. (1989) *Regulated genes in transgenic plants.* Science 244, 174–181.

Bowen, B. (1992). *Anthocyanin genes as visual markers in transformed maize tissues.* In Gallagher, S. R. (ed.) GUS Protocols: Using the GUS gene as a reporter of gene expression. Academic Press. San Diego, Calif. pp. 163–177.

Bureau T. E. and Wessler S. R. (1992) *Tourist: A large family of small inverted repeat elements frequently associated with maize genes.* The Plant Cell 4:1283–1294.

Carlson, D. P. and Ross, J. (1983) *Human b-globin promoter and coding sequences transcribed by RNA polymerase III.* Cell 34:857–864.

Chen, J., Greenblatt, I. M., and Dellaporta, S. L. (1987) *Transposition of Ac from the P locus of maize into unreplicated chromosomal sites.* Genetics 117:101–108.

Chen, J., Greenblatt, I. M., and Dellaporta, S. L. (1992) *Molecular analysis of Ac transposition and DNA replication.* Genetics 130:665–676.

Das, O. P., Messing, J. (1994) *Variegated phenotype and developmental methylation changes of a maize allele originating from epimutation.* Genetics 136:1121–1141.

De Block, M., Botterman, J., Vandewile, M., Docky, J., Thoen, C., Gossele, V., Rao Movva, N., Thompson, C., Van Montagu, M., and Leemans, J. (1987) *Engineering herbicide resistance in plants by expression of a detoxifying enzyme.* EMBO Journal 6:125–135.

Dennis, E., Gerlach, W., Pryor, A., Bennetzen, J., Inglis, A., Llewellyn, D., Sachs, M., Ferl, R. and Peacock, W. (1984) *Molecular characterization of the maize Adhl gene.* Nucl. Acids Res. 12:3983–3990.

Emerson, R. A. (1917) *Genetical studies of variegated pericar in maize.* Genetics 2:1–35.

Fromm, M. (1994) *Production of transgenic maize plants via microprojectile-mediated gene transfer.* In Freering, M. and Walbot, V. (eds), The Maize Handbook. Spring-Verlag, New York. pp. 677–684.

Gallie, D. R. and Young T. E. (1994) *The regulation of gene expression in transformed maize aleurone and endosperm protoplasts.* Plant Physiol. 106:929–939.

Gordon-Kamm, W. J., Spencer, M., Mangano, M. L., Adams, T. R., Daines, R. J., Start, W. G., O'Brien, J. V., Chambers, S. A., Adams, W. R. Jr., Willetts, N. G., Rice, T. B., Mackey, K. J., Krueger, R. W., Kausch, A. P. and Lemaux, P. G. (1990) *Transformation of Maize Cells and Regeneration of Fertile Transgenic Plants.* The Plant Cell 2:603–618.

Grotewold E., Drummond B. J., Bowen B., and Peterson T. (1995) *The myb-homologous P gene controls phlobaphene pigmentation in maize floral organs by directly activating a flavonoid biosynthetic gene subset.* Cell 76:543–553.

Grotewold, E., Athma, P., and Peterson, T. (1991) *Alternatively sliced products of the maize P gene encode proteins with homology to the DNA binding domain of Myb-like transcription factors.* Proc. Natl. Acad. Sci. U.S.A. 88:4587–4591.

Hull, M. W., Erickson, J., Johnston, M. and Engelke, D. R. (1994) *tRNA genes as transcriptional repressor elements.* Molecular and Cellular Biology 14:1266–1277.

Jefferson, R. A., Burgess, S. M. and Hirsh, D. (1986) b-Glucuronidase from Escherichia coli as a gene fusion marker. Proc. Natl. Acad. Sci. U.S.A. 83:8447–8451.

Klein, T. M., Kormstein, L., Sanford, J. C., and Fromm, M. E. (1989) Genetic transformation of maize cells by particle bombardment. Plant Physiol. 91:44044.

Konieczny, A., Voytas, D. F., Cummings, M. P. and Ausubel, F. M. (1991) A superfamily of Arabidopsis thaliana retrotransposons. Genetics 127 (4), 801–809.

Kyozuka J., Olive, M., Peacock, W. J., Dennis, E. S. and Shimamoto K. (1994) Promoter Elements Required for Developmental Expression of the Maize Adh1 gene in Transgenic Rice. The Plant Cell 6:799–810.

Lecheit, C., Peterson, T., Laired, A., Chen, J., Dellaporta, S., Dennis, E., Peacock, W. J., and Starlinger, P. (1989) Isolation and molecular analysis of the maize P locus. Mol. Gen. Genet. 219:225–234.

Ludwig, S. E., Bowen, B., Beach, L., and Wessier, S. R. (1990). A regulatory gene as a novel visible marker for maize transfornation. Science 246:449–450.

Lund G., Das O. P., and Messing J. (1995) Tissue-specific DNase I-sensitive sites of the maize P gene and their changes upon epimutation. The Plant Journal 7(5):797–807.

Moreno, M. A., Chen, J., Greenblatt, I., and Dellaporta, S. L. (1992) Reconstitutional mutagenesis of the maize P gene by short-range Ac transpositions. Genetics 131:939–956.

Peterson, T. (1990) Intragenic transposition of Ac generates a new allele of the maize P gene. Genetics 126:469–476.

Radicella J. P., Brown D., Tolar L. A. and Chandler V. L. (1992) Allelic diversity of the maize B regulatory gene: different leader and promoter sequences of two B alleles determine distinct tissue specificities of anthocyanin production. Genes & Development 6:2152–2164.

Styles, E. D. and Ceska 0. (1977) The genetic control of flavonoid synthesis in maize. Can. J. Genet. Cytol. 19:289–302.

Styles, E. D. and Ceska 0. (1981) P and R control of flavonoids in Bronze coleptiles of maize. Can. J. Genet. Cytol. 23:691–704.

Su, T. Z. and El-Gewely, M. R. (1998) A multisite-directed mutagenesis procedure using T7 DNA polymerase: Application for reconstructing a mammalian gene. Gene 69:81–89.

Linger, E., Parsons, R. L., Schmidt, R. J., Bowen, B., and Roth, B. A. (1993) Dominant negative mutants of Opaque2 suppress transactivation of a 22-IcD zein protein by opaque 2 in maize endosperm cells. Plant Cell 5: 831–841. Voytas D. F., Cummings, M. P., Konieczny, A., Ausubel, F. M. and Rodermel, S. R. (1992) Copia-like retrotransposons are ubiquitous among plants. Proc. Natl. Acad. Sci. U.S.A. 31: 7124–7128.

Walker E. L., Robbins, T. P., Bureau, T. E., Kermicle, J., and Dellaporta, S. L. (1995) Transposon-mediated chromosomal rearrangements and gene duplications in the formation of the maize R-r complex. The EMBO Journal 14: 2350–2363.

Weiher, H., Konig, M., Gruss, P. (1983) Multiple point mutations affecting the Simian virus 40 enhancer. Science 219:626–631.

Christensen, et al. (1992). Maize polyubiquitin genes: structure, thermal perturbation of expression and transcript splicing, and promoter activity following transfer to protoplasts by electroporation. Plant Mol. Biol. 18: 675–689.

Odell, et al. (1985). Identification of DNA sequences required for activity of the cauliflower mosaic virus 53S promoter. Nature 313: 810–812.

Depicker, et al. (1982). Nopaline synthase: transcript mapping and DNA sequence. J. Mol. Appl. Genet. 1: 561–573.

---

What is claimed is:

1. A purified DNA fragment consisting essentially of the nucleotide sequence shown in SEQ ID NO:1.

2. A purified DNA fragment consisting essentially of the nucleotide sequence shown in SEQ ID NO:2.

3. A purified DNA fragment consisting essentially of the nucleotide sequence shown in SEQ ID NO:3.

4. A purified DNA fragment consisting essentially of the nucleotide sequence shown in SEQ ID NO:4.

5. A purified DNA fragment consisting essentially of the nucleotide sequence shown in SEQ ID NO:5.

6. A purified DNA fragment consisting essentially of the nucleotide sequence shown in SEQ ID NO:6.

7. A plant comprising a nucleotide sequence selected from the group consisting of SEQ ID NO:1, SEQ ID NO:2, SEQ ID NO:3, SEQ ID NO:5, and SEQ ID NO:6 wherein said nucleotide sequence is operably linked to a reporter or effector gene and drives expression of said reporter or effector gene in a floral tissued-preferred manner.

8. A plant of claim 7 wherein said plant is maize.

9. A DNA molecule comprising a transcriptional regulatory region which drives floral tissue-preferred gene expression operably linked to a reporter or effector gene, wherein said transcriptional regulatory region consists essentially of a nucleotide sequence selected from the group consisting of SEQ ID NO:1, SEQ ID NO:2, SEQ ID NO:3, SEQ ID NO:5, and SEQ ID NO:6.

10. A DNA molecule of claim 9 wherein said reporter gene encodes β-glucuronidase.

11. A DNA molecule of claim 9 wherein said effector gene encodes a gene product that confers ear mold resistance upon a plant in which said gene product is expressed.

12. A method of generating a transgenic maize plant comprising, in combination, the steps of:

transforming a maize regenerable culture with a DNA molecule comprising a reporter or effector gene operably linked to a transcriptional regulatory region which drives expression of said gene in a floral tissue-preferred manner; and regenerating said maize regenerable culture into a plant;

whereby said maize plant expresses said assayable gene product or effector gene product in a floral-preferred manner; and wherein said transcriptional regulatory region consists essentially of a nucleotide sequence selected from the group consisting of SEQ ID NO.:1, SEQ ID NO.:2, SEQ ID NO.:3, SEQ ID NO.:5, and SEQ ID NO.:6.

13. The method of claim 12 wherein transformation of said regenerable culture comprises particle bombardment.

14. The method of claim 12 wherein said effector gene encodes a gene product that confers ear mold resistance to a maize plant in which said gene product is expressed.

15. A transgenic plant comprising a transcriptional regulatory region consisting essentially of a nucleotide sequence selected from the group consisting of SEQ ID NO.:1, SEQ ID NO.:2, SEQ ID NO.:3, SEQ ID NO.:5, and SEQ ID NO.:6 operably linked to a reporter or effector gene.

16. A transgenic plant of claim 15 wherein said transgenic plant is maize.

17. A transgenic plant of claim 15 wherein said transcriptional regulatory region is operably linked to a reporter gene.

18. A transgenic plant of claim 15 wherein said transcriptional regulatory region is operably linked to a β-glucuronidase reporter gene.

19. A transgenic plant of claim 15 wherein said transcriptional regulatory region is operably linked to an effector gene.

20. A transgenic plant of claim 15 wherein said transcriptional regulatory region is operably linked to a gene encoding a gene product that confers ear mold resistance to a plant in which said gene is expressed.

21. A seed comprising a nucleotide sequence selected from the group consisting of SEQ ID NO.:1, SEQ ID NO.:2, SEQ ID NO.:3, SEQ ID NO.:5, and SEQ ID NO.:6, wherein said nucleotide sequence is operably linked to a reporter or effector gene.

* * * * *

UNITED STATES PATENT AND TRADEMARK OFFICE
CERTIFICATE OF CORRECTION

PATENT NO.    : 5,955,361                                    Page 1 of 1
DATED         : September 21, 1999
INVENTOR(S)   : Xianggan Li, Ben Bowen and Thomas Peterson It is certified that error appears in the above-identified patent and that said Letters Patent is hereby corrected as shown below:

Title page,
Item [73], Assignee, should read -- Pioneer Hi-Bred International, Inc.,
Des Moines, Iowa
Iowa State University Research Foundation
Ames, Iowa --

Figure 5D:
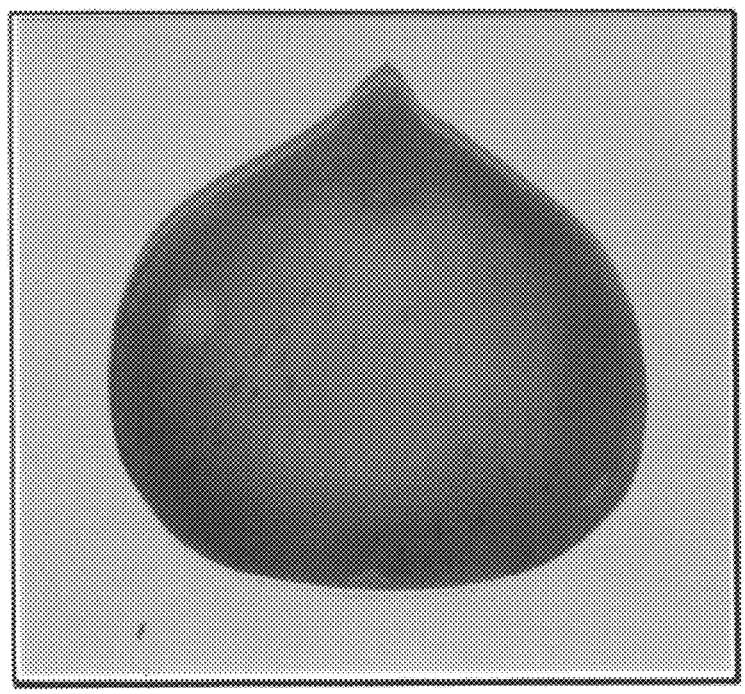
Figure 5E:
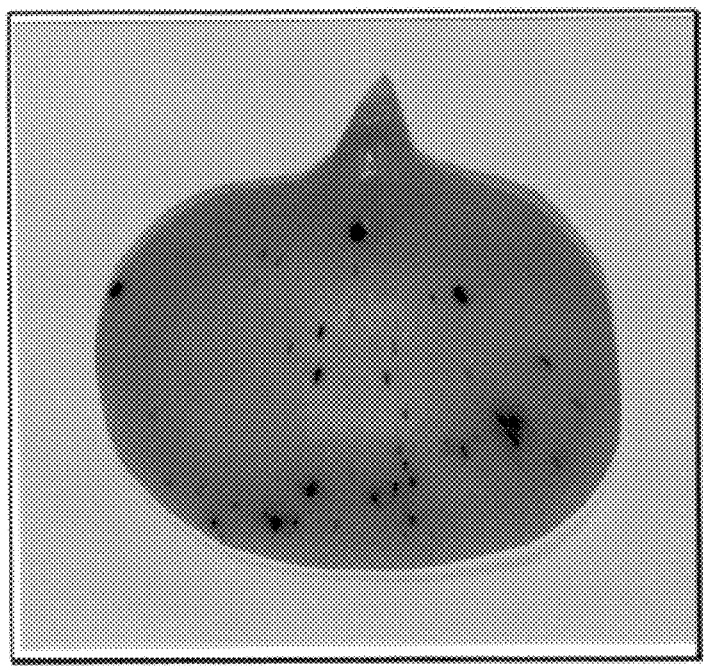
Figure 5F:
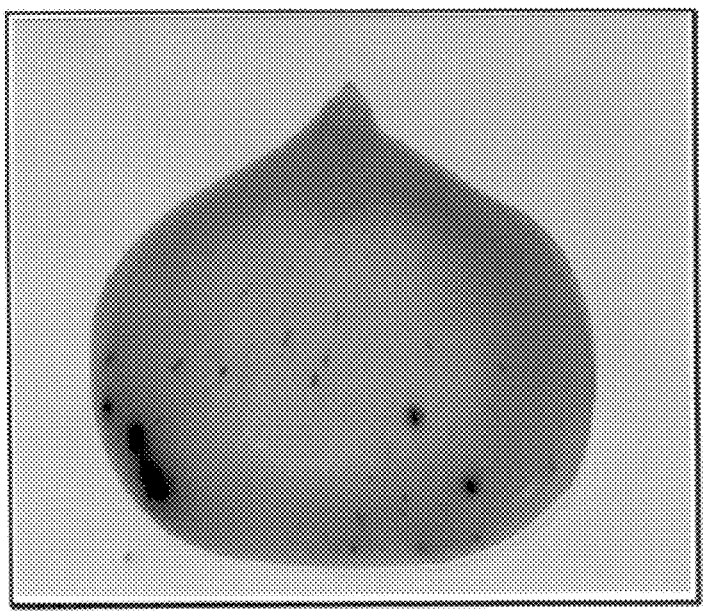

Drawings,
Figure sheet 6 of 13, "FIG.5D" should read -- FIG.5E --.
Figure sheet 7 of 13, "FIG. 5E" should read -- FIG.5D --.

Column 3,
Line 59, "B, C, and F" should read -- B, D, and F --.

Column 12,
Line 31, last word "R65," should read -- R165 --.

Signed and Sealed this

Third Day of September, 2002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
GTCGACGCCA CGCGTCTGGG TTGTGCCAAC GCAACACGAC CTCGGCGCCA TAGCCTATGG      60

CGCCGAGCAA A                                                          71
```

(2) INFORMATION FOR SEQ ID NO:2:

(i) SEQUENCE CHARACTERISTICS:
      (A) LENGTH: 1576 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:2:

```
AAGCTTAGTC GTTCGAATTA AAGAACTAAC CATGGTACAG AAAAGTTAGG TAAAGTATGG      60

CAAGTTCTAA AACTGTTTCT TACACCTGCG GTGCTTCTCA AGAGGCCCTT ATTTCAGCCG     120

TATTCAAAAG CGTTTTTTTC ACCGCAGTAA CAAGGACGGC ATATATCGGC CTGGGATTGC     180

AAGCGAGCAG GCAACGCTGT GCGGGAGTGC GGCCTGCGGG AGTGCGGCCT GCTCGGTTGT     240

GTTATTAAAA TATTTGTTGC AGACATGAGC ATAAAGCTCA TCTAGCCCAC TTGGTAGAGC     300

ACAAGGCTTC TAACCATGTG GTCGTGGGTT CAAGCCCCAT AGTTTGCATT TTTTTTGTTT     360

TTTTGTTTAT GTCGTGGGTT CAAGCCCCAT AGTTCCGCTT AAATTTATTT TCTCGCCTAG     420

ATTTTTTTTT TCACAATTGA AAAAATCGAC CCAAAATATA TGCTCATGTA CTGATCGGCC     480

AATATCTCTG TATGTGAAAG GTTGTGGAGA ATAATAATAA GTAGGGCATG CTGTTTATCA     540

AAGCAAATGT ATATAAGGAA GAAAAAAATG TATAAAAATA TTTATAGTGA TTTAGAAATA     600

GTTAATGATT CGTAATGCAA ATTTTGAATA ATGCACGGAT GACATTTTAT AAAATTACTA     660

CATTGCTTTT GTATTGCACA TGCATGATTT GAGCTAGTCG ATTATTTACG CGCATTTTAA     720

ATTCGGAAAC TGTAGATTGA AATGCGCGCG CATGCAGTGC AAGTATGGAA GGCAACACTA     780

GGCACAACGA CATAAAAAAA ATCTAGGCGA GAAATAAATT TAAGCGGACA CACCAACGAC     840

ATAAACAAAA AAAAACAAAA AAAATGCAAA CTATGGGGTT TGAACCCACG ACCACATGGT     900

TAGAAGCCTT GTGCTCTACC AAGTGGGCTA GATGGGCTTT GTGCTCATGT TTGCAACAAA     960

TATTTTAATA ACACAACCGA GCTCGGCGCC AAGATCTTGG CGCCGAGCTC GGTTCCACGT    1020

CGACGCCACG CGTCTGGGTT GTGCCAACGC AACACGACCT CGGCGCCATA GCCTATGGCG    1080

CCGAGCAAAG GGTCCAAAAC TGCATTTAAA ATTTTTTTAG GTCTAAACGT GATTTTACTT    1140

CTGTTTAAGG GCAAAATACA AACGTGCACT CTGCACTCTA CTAAGCGCTA GTGTACGTAC    1200

GTACGTACTC CGTCCGCTGC TATATTATGG CCGGCCGTGG CGTGCCCTCT CTAGCCAGCA    1260

CAGCACACAC ACTGGAAAGT GCAAGCTGTA GTGAGACCTG CGCGACTGCC AGCGTGTATC    1320

CGCGCGGCAA GGAGCGTAGC GCGCGGTCGT CGGCCCGCAC GGCCACCAAC TCCCTTGGAC    1380

GCACGCGCGC GCGCGACCAG CTGCTAACCG TGCGCAAGTA GTAGTGCGAC TTCGCCGCCG    1440

GCCGGGATCG CTAGCTCGAT CGATCGGCGG GACCACATAC GACTCCGGTG TGGCCAGCGG    1500

CGGCCGGGCC GGGGAACGCA CGTGCTGCGA GCGAGCGAGG GCAGACGCTA GCTGTTGCCG    1560

GGAGCTAGCC GGATCC                                                   1576

(2) INFORMATION FOR SEQ ID NO:3:

(i) SEQUENCE CHARACTERISTICS:
        (A) LENGTH: 1827 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

GTCGACGGCC ATATGCATGC ATGCATGGGT GATCGGTGAC GTAGCAGCGG CTTCTCGGTG      60

TGTGTCGTCG CTAGCTGGCC AGTGTGCGGT CGAGTTTGTT CGTGCTAATT AAACGAGGAG     120

AAATCATTGT TTGCAGGCGC CACCTGATGA TCGAAGCGGA TTACTCACCG CCCTCGACTG     180

TTCGATGCCT GCCGCGTGGA GCTCTTGCGT ATCTAACGCT CCCACGACAA TCACCCTTCC     240

AGACGGCTCG AATTACATAC GACAGGATCG GCTCCGCTCT ACTCCGTTCT GTTCGCTTCT     300

GCTTTAGGTG CGTGCCTAGC AGATGGTGAG GCGGCGTCGC GCGGCCCTCC CGACGGCTCG     360

CCGGCCGCGC TACGGGGCCT GCTGCAGCAG CCCCTCCTCC ACGCCTGTAA AAGAGCTTTG     420
```

```
TATTTACCTG TTTGTTTGTG CTTTTGTGCA ATGGAATAAA CAATGATATT ATACTGAATA        480

AACATGAATG TTCTGAGACA AATCATTTCG AACTGCAATT GCAATATTTA ATGACATTGA        540

ACTGGGATTG TCAGCTTTGA ATGAACCGGC CAGCTCGTAC TCCATTATTA CAAAGTTACT        600

AGTAGAATTT CTACACGTG AACTTAAATT TTCCAAGTAT GCTACTACTG ATTGTACTCA         660

AGTGTCCCTG TGCACACTCG CATGAGCTAG CATCTGCCGA TGCTCTTTTC CTTCTCTTCC        720

AGTTGGTAGT CTTTTCGGTC TGAAATCTAG ATTGTCAGAT ATTCTCGTTA TTTGGCAATC        780

CATCAAACTG CAACTTCTTA ACTACTGAAG CAGCACCTTG ATCAACTCCA AGTAAAAGAC        840

TTGTGTATCC TCAACCTATG TGGAGAGCTC GATCCATCGC CCAACCCCAA CCTATGTGGT        900

TTGTTGCCTG CTCCCACTTT GTCTTGCCAT CCATGTGTCG GCTACTGCTC CCTTGCGCAA        960

TTATTATTCA AGTTTGGCGA TCCAAGAGCC CCCAAGATAT GTGTGTGCTC GACTGCTCGC       1020

TCGCTGCCGT CGCGTGGGTC TTCGTTCAGA TGGCCAAATA ATTGCAGGGA GAGGGAGGGA       1080

CCAATCGCCG CTGCAGCAGT GCCCAGTGAG TGGTGCCACC ACGCGCTTGT CTTGTCAGCT       1140

TGCGGAGAGC CACCACATGC TTCCCACATG ATGAGCCCCA GGCAGGCTGA CGACGTCTCA       1200

CCGGCTCACA CCTCCTCCTC CGTCCTCAAA ACCAAAGCGT TGCGTTGCAT GCTTTGTTTC       1260

GTTCCGCACG TCGACGCCAC GCGTCTGGGT TGTGCCAACG CAACACGACC TCGGCGCCAT       1320

AGCCTATGGC GCCGAGCAAA GGGTCCAAAA CTGCATTTAA AATTTTTTTA GGTCTAAACG       1380

TGATTTTACT TCTGTTTAAG GGCAAAATAC AAACGTGCAC TCTGCACTCT ACTAAGCGCT       1440

AGTGTACGTA CGTACGTACT CCGTCCGCTG CTATATTATG GCCGGCCGTG GCGTGCCCTC       1500

TCTAGCCAGC ACAGCACACA CACTGGAAAG TGCAAGCTGT AGTGAGACCT GCGCGACTGC       1560

CAGCGTGTAT CCGCGCGGCA AGGAGCGTAG CGCGCGGTCG TCGGCCCGCA CGGCCACCAA       1620

CTCCCTTGGA CGCACGCGCG CGCGCGACCA GCTGCTAACC GTGCGCAAGT AGTAGTGCGA       1680

CTTCGCCGCC GGCCGGGATC GCTAGCTCGA TCGATCGGCG GGACCACATA CGACTCCGGT       1740

GTGGCCAGCG GCGGCCGGGC CGGGGAACGC ACGTGCTGCG AGCGAGCGAG GGCAGACGCT       1800

AGCTGTTGCC GGGAGCTAGC CGGATCC                                          1827

(2) INFORMATION FOR SEQ ID NO:4:

(i) SEQUENCE CHARACTERISTICS:
            (A) LENGTH: 2441 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:4:

AAGCTTGATA GAGATATAAA CTCTTGTTGG CGACTCTGAT ATTTTTAACG GGAGGCATAA         60

AAAAATGTGC AATCTTCTCG CTGGTTCTTA TCCAAAATCC TTTGCAATGA TGCTCACGTG        120

AGGACTAACC GTACGGTTAG ATAATTCCAT GTATTGCTCT ATATCTTAAA GATGTGATTT        180

ATAATAAATT AATTTAAATA AATAAATATA AACATTACTT CTAAATCTTT TAACCGATGA        240

GTTCTACTCT CTCGGACCGA GAGAGCACAA CTTCTAGAGT TTACAACCCA GCCACGTGCC        300

TACTTAGATC ATGTTTGGAA GCACCTAGTT TTTAAGAAAT CGGTGTGCTT CCAAACATGT        360

CAATTTCTAC TTTAGTTTCT AGAAATTGTA TTCCATGTTT CTTAAGAAAC ACTAAGAAGT        420

TAGCCAACCC CTTGCTAAAA CCCATTTGTG CATGACAATT TAAGTACCAC ACTTAGAGCT        480

TGTTCGGTTC TACCTCAATC CATGGATTGA GGGGGGATTG AGAGGGTTTC AATCCCTAGT        540
```

-continued

| | |
|---|---|
| AAATCAAAAT CTCCCTCAAT CCGTATCAAT CCCCTCCAAT CCATATGGAT TGAAAATAAC | 600 |
| CAAACAGTCC CTAGCAGTCC CTAGTGAGTT TAGTGAAAAT TACGATAATT GCCACCGCTA | 660 |
| CCCTCAATGC ATGCACTGTC CTATTTAAAT GTATAATCAT CATTTAAAAT TTTAAAATAA | 720 |
| TAATATAAGT TTATTCTATA GTTAAAGTTG GCATCAAACA AAAAAAGATA AATGAATCAA | 780 |
| TTATTTTTAA AATGGAGTGA GAGCTGGCTT ACAAACACGT ACTTTTAGTT TGTTTCCATA | 840 |
| AACCAGTTTC TAGAAACTGA AGATTAAGAG TCTGTTTGGT TCGTGACTAG CTGTGAGAGC | 900 |
| TGGCTTACAA ACACGTACTT TTAGTTTGTT TCCATAAACC AGTTTCTAGA AACTGAAGAT | 960 |
| TAAGAGTCTG TTTGGTTCGT GACTAACTGC GTTACACTTT GTCTAAGCTT AGTCGTTCGA | 1020 |
| ATTAAAGAAC TAACCATGGT ACAGAAAAGT TAGGTAAAGT ATGGCAAGTT CTAAAACTGT | 1080 |
| TTCTTACACC TGCGGTGCTT CTCAAGAGGC CCTTATTTCA GCCGTATTCA AAAGCGTTTT | 1140 |
| TTTCACCGCA GTAACAAGGA CGGCATATAT CGGCCTGGGA TTGCAAGCGA GCAGGCAACG | 1200 |
| CTGTGCGGGA GTGCGGCCTG CGGGAGTGCG GCCTGCTCGG TTGTGTTATT AAAATATTTG | 1260 |
| TTGCAGACAT GAGCATAAAG CTCATCTAGC CCACTTGGTA GAGCACAAGG CTTCTAACCA | 1320 |
| TGTGGTCGTG GGTTCAAGCC CCATAGTTTG CATTTTTTTT GTTTTTTTGT TTATGTCGTG | 1380 |
| GGTTCAAGCC CCATAGTTCC GCTTAAATTT ATTTTCTCGC CTAGATTTTT TTTTTCACAA | 1440 |
| TTGAAAAAAT CGACCCAAAA TATATGCTCA TGTACTGATC GGCCAATATC TCTGTATGTG | 1500 |
| AAAGGTTGTG GAGAATAATA ATAAGTAGGG CATGCTGTTT ATCAAAGCAA ATGTATATAA | 1560 |
| GGAAGAAAAA AATGTATAAA AATATTTATA GTGATTTAGA AATAGTTAAT GATTCGTAAT | 1620 |
| GCAAATTTTG AATAATGCAC GGATGACATT TTATAAAATT ACTACATTGC TTTTGTATTG | 1680 |
| CACATGCATG ATTTGAGCTA GTCGATTATT TACGCGCATT TTAAATTCGG AAACTGTAGA | 1740 |
| TTGAAATGCG CGCGCATGCA GTGCAAGTAT GGAAGGCAAC ACTAGGCACA ACGACATAAA | 1800 |
| AAAAATCTAG GCGAGAAATA AATTTAAGCG GACACACCAA CGACATAAAC AAAAAAAAAC | 1860 |
| AAAAAAAATG CAAACTATGG GGTTTGAACC CACGACCACA TGGTTAGAAG CCTTGTGCTC | 1920 |
| TACCAAGTGG GCTAGATGGG CTTTGTGCTC ATGTTTGCAA CAAATATTTT AATAACACAA | 1980 |
| CCGAGCTCGG CGCCAAGATC TTGGCGCCGA GCTCGGTTCC ACGTCGACGC CACGCGTCTG | 2040 |
| GGTTGTGCCA ACGCAACACG ACCTCGGCGC CATAGCCTAT GGCGCCGAGC AAAGGGTCCA | 2100 |
| AAACTGCATT TAAAATTTTT TTAGGTCTAA ACGTGATTTT ACTTCTGTTT AAGGGCAAAA | 2160 |
| TACAAACGTG CACTCTGCAC TCTACTAAGC GCTAGTGTAC GTACGTACGT ACTCCGTCCG | 2220 |
| CTGCTATATT ATGGCCGGCC GTGGCGTGCC CTCTCTAGCC AGCACAGCAC ACACACTGGA | 2280 |
| AAGTGCAAGC TGTAGTGAGA CCTGCGCGAC TGCCAGCGTG TATCCGCGCG GCAAGGAGCG | 2340 |
| TAGCGCGCGG TCGTCGGCCC GCACGGCCAC CAACTCCCTT GGACGCACGC GCGCGCGCGA | 2400 |
| CCAGCTGCTA ACCGTGCGCA AGTAGTAGTG CGACTTCGCC G | 2441 |

(2) INFORMATION FOR SEQ ID NO:5:

(i) SEQUENCE CHARACTERISTICS:
        (A) LENGTH: 2940 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

| | |
|---|---|
| AAGCTTCTTC TATCTATCTC CAAAGCTGAA GAACCTAAAG TAGCTTTTGT TTTTTGATCT | 60 |
| CCATGTGCCT TTAGATAGTT TCTAGCCCCC TCAATCTCCA AATTGACACC ATCCTATTCA | 120 |

```
ACCAATAACT TTACGACTGT TCTCTTCTCA TGCCTTCAGT TGTTAGATTC GATATGCTTG      180

TCTTCACTAT AGCCTTGTTA TTCGACATTG TTATGACAAT CTGTTACGCT AACATCCCTT      240

ACACTTCCAG GAGTCATGGT TATGGTCGTT GTGAGTTCAC CGTAGATGAA TGCCAAATGT      300

TGGATACCTA TCAAATTTTT GAAAAGAACA ACATTAGGAC AACAACATTA ATTTAAAAAT      360

CCTTCTTTCT TACAAAGGTT TTAGAAGGAG AAGGTATCAA ATAGAGTTGT GACTATTTTA      420

ACAAGTGTGT AAAATAAGAA CAACAATAAG AGTTCGACAC CATTTGATTG ATCATTACTC      480

CAATGGTTAT AGTTTCCACT CATATATATG TGAGAATGTT ATAGACAGAT ACTAATGGAG      540

GAGCTTTAGT ACATTAGTAC CATCAAAGGC TCTTCACACA CAAGAATGCC ACCAACGATA      600

TTTATAAATG GTCAATCCCT TTAGCTGTGG CATTGTTTAT CTATTTATAT GGATGTGTCC      660

ATATACACCT TTGTACGAAA TTACAATTTT ACCCTAGTTA CTACATGGTA ATTCTTCGTA      720

AATGAGGGAG TATATTTTTG ACATTTTTTA CAACCTTGAC ATGTCATGTA CACATTTTCT      780

TTACCTTGGA GACCTTTGTT TTCTTTATCC GAAGCCTTTT TTGGCCATGT TAAGTCACAC      840

TTTCTTCTTC TCCGGCTTCG TGCATGCTTC AAATTATCTG ACGTTCGAAG CTCCCCTAAG      900

CATGATGGCC TTTGGCTTTG ATTAAGAAAA TGTCTAGACC TTGATTTTGT CGATATGGAC      960

CTTCGGCCAG AGGCATTTTC CCCAATAGGT GACTACCCCA ACCATGAGTA TTGTAGCTAT     1020

TGCTAGTAGT GTTGGAGTGA TGGCAGGATC CCCTAACTTG TGGACCTATA TGTGAGGAGA     1080

TGCCATATAA GTGGCTTGTT AAAGTGTCGT TGTAGGACAC CTGACTCATA AGGAGCTGGA     1140

ACTAGGCAAT CTATTCTGCA AATTATGGTC TCTAATATCC GCCTTGTCAA AAATCCATGT     1200

AACAAATAAA CTATTCATGT ATAACTATAG TTTTAAATAA GTATAATACT ATCCCTACCG     1260

CAAATAGTTA CACAACCTAG GTTCTAAACA TATCCATTAG CCTAACAACT AAAATAGAAA     1320

TGTAAAGCAT CCAAACAAGA TATACAATAT AAATGCAAAA TTTTAAGCTT AGTCGTTCGA     1380

ATTAAAGAAC TAACCATGGT ACAGAAAAGT TAGGTAAAGT ATGGCAAGTT CTAAAACTGT     1440

TTCTTACACC TGCGGTGCTT CTCAAGAGGC CCTTATTTCA GCCGTATTCA AAAGCGTTTT     1500

TTTCACCGCA GTAACAAGGA CGGCATATAT CGGCCTGGGA TTGCAAGCGA GCAGGCAACG     1560

CTGTGCGGGA GTGCGGCCTG CGGGAGTGCG GCCTGCTCGG TTGTGTTATT AAAATATTTG     1620

TTGCAGACAT GAGCATAAAG CTCATCTAGC CCACTTGGTA GAGCACAAGG CTTCTAACCA     1680

TGTGGTCGTG GGTTCAAGCC CCATAGTTTG CATTTTTTTT GTTTTTTTGT TTATGTCGTG     1740

GGTTCAAGCC CCATAGTTCC GCTTAAATTT ATTTTCTCGC CTAGATTTTT TTTTTCACAA     1800

TTGAAAAAAT CGACCCAAAA TATATGCTCA TGTACTGATC GGCCAATATC TCTGTATGTG     1860

AAAGGTTGTG GAGAATAATA ATAAGTAGGG CATGCTGTTT ATCAAAGCAA ATGTATATAA     1920

GGAAGAAAAA AATGTATAAA AATATTTATA GTGATTTAGA AATAGTTAAT GATTCGTAAT     1980

GCAAATTTTG AATAATGCAC GGATGACATT TTATAAAATT ACTACATTGC TTTTGTATTG     2040

CACATGCATG ATTTGAGCTA GTCGATTATT TACGCGCATT TTAAATTCGG AAACTGTAGA     2100

TTGAAATGCG CGCGCATGCA GTGCAAGTAT GGAAGGCAAC ACTAGGCACA ACGACATAAA     2160

AAAAATCTAG GCGAGAAATA AATTTAAGCG GACACACCAA CGACATAAAC AAAAAAAAAC     2220

AAAAAAAATG CAAACTATGG GGTTTGAACC CACGACCACA TGGTTAGAAG CCTTGTGCTC     2280

TACCAAGTGG GCTAGATGGG CTTTGTGCTC ATGTTTGCAA CAAATATTTT AATAACACAA     2340

CCGAGCTCGG CGCCAAGATC TTGGCGCCGA GCTCGGTTCC ACGTCGACGC CACGCGTCTG     2400

GGTTGTGCCA ACGCAACACG ACCTCGGCGC CATAGCCTAT GGCGCCGAGC AAAGGGTCCA     2460

AAACTGCATT TAAAATTTTT TTAGGTCTAA ACGTGATTTT ACTTCTGTTT AAGGGCAAAA     2520
```

```
TACAAACGTG CACTCTGCAC TCTACTAAGC GCTAGTGTAC GTACGTACGT ACTCCGTCCG    2580

CTGCTATATT ATGGCCGGCC GTGGCGTGCC CTCTCTAGCC AGCACAGCAC ACACACTGGA    2640

AAGTGCAAGC TGTAGTGAGA CCTGCGCGAC TGCCAGCGTG TATCCGCGCG GCAAGGAGCG    2700

TAGCGCGCGG TCGTCGGCCC GCACGGCCAC CAACTCCCTT GGACGCACGC GCGCGCGCGA    2760

CCAGCTGCTA ACCGTGCGCA AGTAGTAGTG CGACTTCGCC GCCGGCCGGG ATCGCTAGCT    2820

CGATCGATCG GCGGGACCAC ATACGACTCC GGTGTGGCCA GCGGCGGCCG GGCCGGGGAA    2880

CGCACGTGCT GCGAGCGAGC GAGGGCAGAC GCTAGCTGTT GCCGGGAGCT AGCCGGATCC    2940

(2) INFORMATION FOR SEQ ID NO:6:

(i) SEQUENCE CHARACTERISTICS:
        (A) LENGTH: 4370 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GAATTCAAAA TGATTTGGTT TGGCCAAACC GGTCGGTTTT TACCGGTTTC CACCGGTTTA      60

CCGACGGTAA ACCGTTACCG GTGGGGGGCG GTTTTTACAT CTAAAACGGT TTTGTAAACC     120

GTGCCAGTGA GTGGTGCCAC CACGCGCTTG TCTTGTCAGC TTGCGGAGAG CCACCACATG     180

CTTCCCACAT GATGAGCCCC AGGCAGGCTG ACGACGTCTC ACCGGCTCAC ACCTCCTCCT     240

CCGTCCTCAA AACCAAAGCG TTGCGTTGCA TGCTTTGTTT CGTTCCGCAC GTCGACGGCC     300

ATATGCATGC ATGCATGGGT GATCGGTGAC GTAGCAGCGG CTTCTCGGTG TGTGTCGTCG     360

CTAGCTGGCC AGTGTGCGGT CGAGTTTGTT CGTGCTAATT AAACGAGGAG AAATCATTGT     420

TTGCAGGCGC CACCTGATGA TCGAAGCGGA TTACTCACCG CCCTCGACTG TTCGATGCCT     480

GCCGCGTGGA GCTCTTGCGT ATCTAACGCT CCCACGACAA TCACCCTTCC AGACGGCTCG     540

AATTACATAC GACAGGATCG GCTCCGCTCT ACTCCGTTCT GTTCGCTTCT GCTTTAGGTG     600

CGTGCCTAGC AGATGGTGAG GCGGCGTCGC GCGGCCCTCC CGACGGCTCG CCGGCCGCGC     660

TACGGGGCCT GCTGCAGCAG CCCCTCCTCC ACGCCTGTAA AAGAGCTTTG TATTTACCTG     720

TTTGTTTGTG CTTTTGTGCA ATGGAATAAA CAATGATATT ATACTGAATA AACATGAATG     780

TTCTGAGACA AATCATTTCG AACTGCAATT GCAATATTTA ATGACATTGA ACTGGGATTG     840

TCAGCTTTGA ATGAACCGGC CAGCTCGTAC TCCATTATTA CAAAGTTACT AGTAGAATTT     900

TCTACACGTG AACTTAAATT TTCCAAGTAT GCTACTACTG ATTGTACTCA AGTGTCCCTG     960

TGCACACTCG CATGAGCTAG CATCTGCCGA TGCTCTTTTC CTTCTCTTCC AGTTGGTAGT    1020

CTTTTCGGTC TGAAATCTAG ATTGTCAGAT ATTCTCGTTA TTTGGCAATC CATCAAACTG    1080

CAACTTCTTA ACTACTGAAG CAGCACCTTG ATCAACTCCA AGTAAAAGAC TTGTGTATCC    1140

TCAACCTATG TGGAGAGCTC GATCCATCGC CCAACCCCAA CCTATGTGGT TTGTTGCCTG    1200

CTCCCACTTT GTCTTGCCAT CCATGTGTCG GCTACTGCTC CCTTGCGCAA TTATTATTCA    1260

AGTTTGGCGA TCCAAGAGCC CCCAAGATAT GTGTGTGCTC GACTGCTCGC TCGCTGCCGT    1320

CGCGTGGGTC TTCGTTCAGA TGGCCAAATA ATTGCAGGGA GAGGGAGGGA CCAATCGCCG    1380

CTGCAGCAGT GCCCAGTGAG TGGTGCCACC ACGCGCTTGT CTTGTCAGCT TGCGGAGAGC    1440

CACCACATGC TTCCCACATG ATGAGCCCCA GGCAGGCTGA CGACGTCTCA CCGGCTCACA    1500

CCTCCTCCTC CGTCCTCAAA ACCAAAGCGT TGCGTTGCAT GCTTTGTTTC GTTCCGCACG    1560
```

```
TCGACGGCCA TATGCATGCA TGCATGGGTG ATCGGTGACG TAGCAGCGGC TTCTCGGTGT    1620

GTCGTCGCTA GCTGGCCAGT GTGCGGTCGA GTTTGTTCGT GCTAATTAAA CGAGGAGAAA    1680

TCATTGTTTG CAGGCGCCAC CTGATGATCG AAGCGGATTA CTCACCGCCC TCGGCTGTTC    1740

GATGCCATCA TGATAATTTG TCACTTGCAT GCACGGATCG CGACGCGATG CGATCGAGTA    1800

GCGGCAAACT CATCAACGTG CTGTTCCAGG GGCTTCGGTT GGTGTTGCTA TACTCTGAGA    1860

TACTGTGCAT TGTATGTCAA AAACCTCGCT GTTAGATACT GACTACTGTG TGACCCGGTG    1920

AATGAATAGT ACTTCAATAA TATATATATG CTTGTTTAAG TTAACTGGCA CGTATATATG    1980

CATGTACTTG TATCTTTTAT GGGAAAAGAC AACACATATT TAATTAAATT CTGAGCTCTT    2040

AGACTTGTAC TGAGCTAATT CTCTAATTGA CCACTGGCGG AGGCAGCACA AACAAACCGG    2100

TTGTATCTTG GATGAAGGGG GACCGGAGTC CCCGTCCACC TTAGATATGA CACTGATGTC    2160

GAAAGCCATT GGCTATATGG ATGTACTCAT CCATCTTCTA AAACAACTTC TCTATAGGAT    2220

ATTTAGAGGA TTTTTAGCAA AGTATTAAGA GCATGAAACA ATTTTGAGCC TCTCGAGTCT    2280

CGATGATTAC CTCAATGACT ACTTCATCTG GCACTCATAT ATTCTAATCC AAACAAACCT    2340

TCATATATAT CTTTTGGAGG GATTCGTCTA CCTCTTGGGC TTATTGAGCA ATGCATATGT    2400

CATAAGTGGT TTGCTTGGAA AGCCTTGAAA ACTTGTAATC AACTGGTTCT TGAGTTTGTT    2460

CACATGTATT TACCAATCTA GGCGAAGGTA CAGGTACCAA GTCAAGGTA TTCCTCTTGC     2520

AACCATGATG AATGACTTGG CCAGGACCAC CGTGTTTCCA CTGAAGGATG TAATAGCTGC    2580

TTCATAGCTC ATGAGAATTT TCTTCGGATC AGACTGCCCA TCATAAGATG GGAAGCAAAT    2640

GTTGCTTAAT TATGAAACAT GCCAAGGGAC TAACTGTAAA TCCCTTGAGA GTGGCCTTGC    2700

TCTTCTTGGA AGACGGTTCT TATGTTGAGA CATCTAGAGT GTTTTTTGTC TTTGTCAACA    2760

TCGTCTTCTC TTCTCATATG ATAAAGCTCT TCAGAAGCTT AGTCGTTCGA ATTAAAGAAC    2820

TAACCATGGT ACAGAAAAGT TAGGTAAAGT ATGGCAAGTT CTAAAACTGT TTCTTACACC    2880

TGCGGTGCTT CTCAAGAGGC CCTTATTTCA GCCGTATTCA AAAGCGTTTT TTTCACCGCA    2940

GTAACAAGGA CGGCATATAT CGGCCTGGGA TTGCAAGCGA GCAGGCAACG CTGTGCGGGA    3000

GTGCGGCCTG CGGGAGTGCG GCCTGCTCGG TTGTGTTATT AAAATATTTG TTGCAGACAT    3060

GAGCATAAAG CTCATCTAGC CCACTTGGTA GAGCACAAGG CTTCTAACCA TGTGGTCGTG    3120

GGTTCAAGCC CCATAGTTTG CATTTTTTTT GTTTTTTTGT TTATGTCGTG GGTTCAAGCC    3180

CCATAGTTCC GCTTAAATTT ATTTTCTCGC CTAGATTTTT TTTTTCACAA TTGAAAAAAT    3240

CGACCCAAAA TATATGCTCA TGTACTGATC GGCCAATATC TCTGTATGTG AAAGGTTGTG    3300

GAGAATAATA ATAAGTAGGG CATGCTGTTT ATCAAAGCAA ATGTATATAA GGAAGAAAAA    3360

AATGTATAAA AATATTTATA GTGATTTAGA AATAGTTAAT GATTCGTAAT GCAAATTTTG    3420

AATAATGCAC GGATGACATT TTATAAAATT ACTACATTGC TTTTGTATTG CACATGCATG    3480

ATTTGAGCTA GTCGATTATT TACGCGCATT TTAAATTCGG AAACTGTAGA TTGAAATGCG    3540

CGCGCATGCA GTGCAAGTAT GGAAGGCAAC ACTAGGCACA ACGACATAAA AAAAATCTAG    3600

GCGAGAAATA AATTTAAGCG GACACACCAA CGACATAAAC AAAAAAAAAC AAAAAAAATG    3660

CAAACTATGG GGTTTGAACC CACGACCACA TGGTTAGAAG CCTTGTGCTC TACCAAGTGG    3720

GCTAGATGGG CTTTGTGCTC ATGTTTGCAA CAAATATTTT AATAACACAA CCGAGCTCGG    3780

CGCCAAGATC TTGGCGCCGA GCTCGGTTCC ACGTCGACGC CACGCGTCTG GGTTGTGCCA    3840

ACGCAACACG ACCTCGGCGC CATAGCCTAT GGCGCCGAGC AAAGGGTCCA AAACTGCATT    3900

TAAAATTTTT TTAGGTCTAA ACGTGATTTT ACTTCTGTTT AAGGGCAAAA TACAAACGTG    3960
```

-continued

```
CACTCTGCAC TCTACTAAGC GCTAGTGTAC GTACGTACGT ACTCCGTCCG CTGCTATATT        4020

ATGGCCGGCC GTGGCGTGCC CTCTCTAGCC AGCACAGCAC ACACACTGGA AAGTGCAAGC        4080

TGTAGTGAGA CCTGCGCGAC TGCCAGCGTG TATCCGCGCG GCAAGGAGCG TAGCGCGCGG        4140

TCGTCGGCCC GCACGGCCAC CAACTCCCTT GGACGCACGC GCGCGCGCGA CCAGCTGCTA        4200

ACCGTGCGCA AGTAGTAGTG CGACTTCGCC GCCGGCCGGG ATCGCTAGCT CGATCGATCG        4260

GCGGGACCAC ATACGACTCC GGTGTGGCCA GCGGCGGCCG GGCCGGGGAA CGCACGTGCT        4320

GCGAGCGAGC GAGGGCAGAC GCTAGCTGTT GCCGGGAGCT AGCCGGATCC                   4370
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

```
GCCGCCGTTA CATTACATTC T                                                    21
```

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

```
CGTCGTCAGC CTGCCTGG                                                        18
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

```
CACGGTTTAC AAAACGG                                                         17
```